(12) United States Patent
Stotz et al.

(10) Patent No.: US 12,728,255 B2
(45) Date of Patent: Sep. 8, 2026

(54) SEALED MICROPUMP

(71) Applicant: KARDION GMBH, Stuttgart (DE)

(72) Inventors: Ingo Stotz, Ditzingen (DE); Johannes Bette, Stuttgart (DE); David Minzenmay, Stuttgart (DE); Fabian Eiberger, Uhldingen-Mühlhofen (DE)

(73) Assignee: KARDION GMBH, Stuttgart (DE)

( * ) Notice: Subject to any disclaimer, the term of this patent is extended or adjusted under 35 U.S.C. 154(b) by 1095 days.

(21) Appl. No.: 17/274,585

(22) PCT Filed: Sep. 26, 2019

(86) PCT No.: PCT/EP2019/076002
§ 371 (c)(1),
(2) Date: Feb. 9, 2022

(87) PCT Pub. No.: WO2020/064911
PCT Pub. Date: Apr. 2, 2020

(65) Prior Publication Data

US 2022/0241580 A1 Aug. 4, 2022

(30) Foreign Application Priority Data

Sep. 28, 2018 (DE) ..................... 10 2018 216 695.1

(51) Int. Cl.
*A61M 60/804* (2021.01)
*A61M 60/126* (2021.01)
(Continued)

(52) U.S. Cl.
CPC ........ *A61M 60/804* (2021.01); *A61M 60/126* (2021.01); *A61M 60/174* (2021.01);
(Continued)

(58) Field of Classification Search
CPC .............. A61M 60/804; A61M 60/126; A61M 60/174; A61M 60/216; A61M 60/416;
(Continued)

(56) References Cited

U.S. PATENT DOCUMENTS 2,254,698 A 9/1941 Hansen, Jr.
2,310,923 A * 2/1943 Bean ....................... F16C 17/14 384/441
(Continued)

FOREIGN PATENT DOCUMENTS

AU 7993698 2/1999
AU 2002308409 12/2005
(Continued)

OTHER PUBLICATIONS

M.J. Neale; "The Tribology Handbook;" 1999, Butterworth-Heinemann, Second Edition (Year: 1999).*
(Continued)

*Primary Examiner* — Jennifer Pitrak McDonald
*Assistant Examiner* — Christopher J Mutchler
(74) *Attorney, Agent, or Firm* — KNOBBE, MARTENS OLSON & BEAR, LLP

(57) ABSTRACT

A sealed micropump includes an integrated motor and at least one impeller for generating fluid flow inside a housing of the micropump. The impeller includes a radial sliding bearing with a spider bearing for supporting an impeller pin of the impeller inside the housing. The impeller pin includes a sheathing of a material different from a material of the spider bearing.

15 Claims, 3 Drawing Sheets

(51) Int. Cl.
*A61M 60/174* (2021.01)
*A61M 60/216* (2021.01)
*A61M 60/416* (2021.01)
*A61M 60/81* (2021.01)
*A61M 60/824* (2021.01)
*A61M 60/825* (2021.01)
*A61M 60/827* (2021.01)
*F04D 7/04* (2006.01)
*F04D 13/06* (2006.01)
*F04D 29/22* (2006.01)

(52) U.S. Cl.
CPC ........ *A61M 60/216* (2021.01); *A61M 60/416* (2021.01); *A61M 60/81* (2021.01); *A61M 60/824* (2021.01); *A61M 60/825* (2021.01); *A61M 60/827* (2021.01); *F04D 7/04* (2013.01); *F04D 13/0633* (2013.01); *F04D 29/22* (2013.01)

(58) Field of Classification Search
CPC .. A61M 60/81; A61M 60/824; A61M 60/825; A61M 60/827; F04D 7/04; F04D 13/0633; F04D 29/22; F04D 29/047; F04D 29/026
See application file for complete search history.

(56) References Cited

U.S. PATENT DOCUMENTS 3,085,407 A 4/1963 Tomlinson
3,505,987 A 4/1970 Heilman
3,568,659 A 3/1971 Karnegis
3,614,181 A 10/1971 Meeks
3,747,998 A 7/1973 Klein et al.
3,807,813 A 4/1974 Milligan
3,995,617 A 12/1976 Watkins et al.
4,115,040 A 9/1978 Knorr
4,245,622 A 1/1981 Hutchins, IV
4,471,252 A 9/1984 West
4,522,194 A 6/1985 Normann
4,625,712 A 12/1986 Wampler
4,643,641 A 2/1987 Clausen et al.
4,753,221 A 6/1988 Kensey et al.
4,779,614 A 10/1988 Moise
4,785,795 A 11/1988 Singh et al.
4,817,586 A 4/1989 Wampler
4,846,152 A 7/1989 Wampler et al.
4,888,011 A 12/1989 Kung et al.
4,889,131 A 12/1989 Salem et al.
4,895,557 A 1/1990 Moise et al.
4,896,754 A 1/1990 Carlson et al.
4,902,272 A 2/1990 Milder et al.
4,908,012 A 3/1990 Moise et al.
4,927,407 A 5/1990 Dorman
4,943,275 A 7/1990 Stricker
4,944,722 A 7/1990 Carriker et al.
4,968,300 A 11/1990 Moutafis et al.
4,971,768 A 11/1990 Ealba
4,985,014 A 1/1991 Orejola
5,044,897 A 9/1991 Dorman
5,061,256 A 10/1991 Wampler
5,089,016 A 2/1992 Millner et al.
5,090,957 A 2/1992 Moutafis et al.
5,112,292 A 5/1992 Hwang et al.
5,112,349 A 5/1992 Summers et al.
5,116,305 A 5/1992 Milder et al.
5,195,877 A 3/1993 Kletschka
5,290,227 A 3/1994 Pasque
5,297,940 A 3/1994 Buse
5,313,765 A 5/1994 Martin
5,344,443 A 9/1994 Palma et al.
5,354,271 A 10/1994 Voda
5,376,114 A 12/1994 Jarvik
5,399,145 A 3/1995 Ito et al.
5,405,383 A 4/1995 Barr
5,443,503 A 8/1995 Yamane
5,456,715 A 10/1995 Liotta
5,527,159 A 6/1996 Bozeman, Jr. et al.
5,599,173 A 2/1997 Chen et al.
5,613,935 A 3/1997 Jarvik
5,695,471 A 12/1997 Wampler
5,702,430 A 12/1997 Larson, Jr. et al.
5,720,771 A 2/1998 Snell
5,746,709 A 5/1998 Rom et al.
5,749,855 A 5/1998 Reitan
5,752,976 A 5/1998 Duffin et al.
5,766,207 A 6/1998 Potter et al.
5,831,365 A 11/1998 Keim et al.
5,888,241 A 3/1999 Jarvik
5,888,242 A 3/1999 Antaki et al.
5,904,646 A 5/1999 Jarvik
5,911,685 A 6/1999 Siess et al.
5,921,913 A 7/1999 Siess
5,964,694 A 10/1999 Siess et al.
6,001,056 A 12/1999 Jassawalla et al.
6,007,478 A 12/1999 Siess et al.
6,018,208 A 1/2000 Maher et al.
6,050,975 A 4/2000 Poirier
6,071,093 A 6/2000 Hart
6,116,862 A 9/2000 Rau et al.
6,123,659 A 9/2000 le Blanc et al.
6,135,710 A 10/2000 Araki et al.
6,149,405 A 11/2000 Abe et al.
6,155,969 A 12/2000 Schima et al.
6,158,984 A 12/2000 Cao et al.
6,161,838 A 12/2000 Balsells
6,176,848 B1 1/2001 Rau et al.
6,186,665 B1 2/2001 Maher et al.
6,210,318 B1 4/2001 Lederman
6,217,541 B1 4/2001 Yu
6,220,832 B1 4/2001 Schob
6,227,820 B1 5/2001 Jarvik
6,245,007 B1 6/2001 Bedingham et al.
6,254,359 B1 7/2001 Aber
6,264,205 B1 7/2001 Balsells
6,264,601 B1 7/2001 Jassawalla et al.
6,264,645 B1 7/2001 Jonkman
6,293,752 B1 9/2001 Clague et al.
6,351,048 B1 2/2002 Schob et al.
6,361,292 B1 3/2002 Chang et al.
6,432,136 B1 8/2002 Weiss et al.
6,445,956 B1 9/2002 Laird et al.
6,447,266 B2 9/2002 Antaki et al.
6,527,698 B1 3/2003 Kung et al.
6,530,876 B1 3/2003 Spence
6,533,716 B1 3/2003 Schmitz-Rode et al.
6,540,658 B1 4/2003 Fasciano et al.
6,544,216 B1 4/2003 Sammler et al.
6,579,257 B1 6/2003 Elgas et al.
6,592,620 B1 7/2003 Lancisi et al.
6,595,743 B1 7/2003 Kazatchkov et al.
6,607,368 B1 8/2003 Ross et al.
6,623,475 B1 9/2003 Siess
6,719,791 B1 4/2004 Nüsser et al.
6,794,789 B2 9/2004 Siess et al.
6,841,910 B2 1/2005 Gery
6,879,126 B2 4/2005 Paden et al.
6,912,423 B2 6/2005 Ley et al.
6,942,611 B2 9/2005 Siess
6,949,066 B2 9/2005 Bearnson et al.
6,969,345 B2 11/2005 Jassawalla et al.
7,011,620 B1 3/2006 Siess
7,014,620 B2 3/2006 Kim
7,022,100 B1 4/2006 Aboul-Hosn et al.
7,027,875 B2 4/2006 Siess et al.
7,070,398 B2 7/2006 Olsen et al.
7,070,555 B2 7/2006 Siess
7,083,588 B1 8/2006 Shmulewitz et al.
7,144,364 B2 12/2006 Barbut et al.
7,160,243 B2 1/2007 Medvedev
7,238,151 B2 7/2007 Frazier
7,241,257 B1 7/2007 Ainsworth et al.

(56) References Cited

U.S. PATENT DOCUMENTS 7,264,606 B2 9/2007 Jarvik et al.
7,393,181 B2 7/2008 McBride et al.
7,436,145 B2 10/2008 Gauthier et al.
7,462,019 B1 12/2008 Allarie et al.
7,479,102 B2 1/2009 Jarvik
7,502,648 B2 3/2009 Okubo et al.
7,736,296 B2 6/2010 Siess et al.
7,762,941 B2 7/2010 Jarvik
7,798,952 B2 9/2010 Tansley et al.
7,841,976 B2 11/2010 McBride et al.
7,850,593 B2 12/2010 Vincent et al.
7,878,967 B1 2/2011 Khanal
7,914,436 B1 3/2011 Kung
7,934,909 B2 5/2011 Nuesser et al.
7,959,551 B2 6/2011 Jarvik
7,963,905 B2 6/2011 Salmonsen et al.
7,998,190 B2 8/2011 Gharib et al.
8,012,079 B2 9/2011 Delgado, III
8,075,472 B2 12/2011 Zilbershlag et al.
8,088,059 B2 1/2012 Jarvik
8,114,008 B2 2/2012 Hidaka et al.
8,123,669 B2 2/2012 Siess et al.
RE43,299 E 4/2012 Siess
8,152,845 B2 4/2012 Bourque
8,177,703 B2 5/2012 Smith et al.
8,216,122 B2 7/2012 Kung
8,371,997 B2 2/2013 Shifflette
8,376,926 B2 2/2013 Benkowsi et al.
8,382,695 B1 2/2013 Patel
8,388,565 B2 3/2013 Shifflette
8,419,609 B2 4/2013 Shambaugh, Jr. et al.
8,449,443 B2 5/2013 Rodefeld et al.
8,480,555 B2 7/2013 Kung
8,485,961 B2 7/2013 Campbell et al.
8,512,012 B2 8/2013 Akdis et al.
8,535,211 B2 9/2013 Campbell et al.
8,545,380 B2 10/2013 Farnan et al.
8,562,508 B2 10/2013 Dague et al.
8,585,572 B2 11/2013 Mehmanesh
8,591,393 B2 11/2013 Walters et al.
8,591,538 B2 11/2013 Gellman
8,591,539 B2 11/2013 Gellman
8,597,170 B2 12/2013 Walters et al.
8,617,239 B2 12/2013 Reitan
8,622,949 B2 1/2014 Zafirelis et al.
8,641,594 B2 2/2014 LaRose et al.
8,657,875 B2 2/2014 Kung et al.
8,684,362 B2 4/2014 Balsells et al.
8,684,904 B2 4/2014 Campbell et al.
8,690,749 B1 4/2014 Nunez
8,721,517 B2 5/2014 Zeng et al.
8,727,959 B2 5/2014 Reitan et al.
8,731,664 B2 5/2014 Foster et al.
8,734,331 B2 5/2014 Evans et al.
8,814,933 B2 8/2014 Siess
8,849,398 B2 9/2014 Evans
8,864,642 B2 10/2014 Scheckel
8,864,643 B2 10/2014 Reichenbach et al.
8,864,644 B2 10/2014 Yomtov
8,882,477 B2 11/2014 Fritz, IV et al.
8,888,728 B2 11/2014 Aboul-Hosn et al.
8,894,387 B2 11/2014 White
8,897,873 B2 11/2014 Schima et al.
8,900,060 B2 12/2014 Liebing
8,900,115 B2 12/2014 Bolling et al.
8,932,246 B2 1/2015 Ferrari
8,992,406 B2 3/2015 Corbett
8,992,407 B2 3/2015 Smith et al.
9,028,216 B2 5/2015 Schumacher et al.
9,028,392 B2 5/2015 Shifflette
9,033,863 B2 5/2015 Jarvik
9,091,271 B2 7/2015 Bourque
9,138,518 B2 9/2015 Campbell et al.
9,144,638 B2 9/2015 Zimmermann et al.
9,162,017 B2 10/2015 Evans et al.
9,192,705 B2 11/2015 Yanai et al.
9,199,020 B2 12/2015 Siess
9,265,870 B2 2/2016 Reichenbach et al.
9,297,735 B2 3/2016 Graichen et al.
9,314,556 B2 4/2016 Tuseth
9,327,067 B2 5/2016 Zeng et al.
9,327,068 B2 5/2016 Aboul-Hosn et al.
9,345,824 B2 5/2016 Mohl et al.
9,370,613 B2 6/2016 Hsu et al.
9,371,826 B2 6/2016 Yanai et al.
9,381,286 B2 7/2016 Spence et al.
9,421,311 B2 8/2016 Tanner et al.
9,433,713 B2 9/2016 Corbett et al.
9,440,013 B2 9/2016 Dowling et al.
9,474,840 B2 10/2016 Siess
9,486,566 B2 11/2016 Siess
9,492,601 B2 11/2016 Casas et al.
9,533,084 B2 1/2017 Siess et al.
9,539,378 B2 1/2017 Tuseth
9,550,017 B2 1/2017 Spanier et al.
9,555,173 B2 1/2017 Spanier
9,555,175 B2 1/2017 Bulent et al.
9,556,873 B2 1/2017 Yanai et al.
9,561,313 B2 2/2017 Taskin
9,561,314 B2 2/2017 Aboul-Hosn et al.
9,579,433 B2 2/2017 LaRose et al.
9,585,991 B2 3/2017 Spence
9,592,397 B2 3/2017 Hansen et al.
9,616,157 B2 4/2017 Akdis
9,623,162 B2 4/2017 Graham et al.
9,623,163 B1 4/2017 Fischi
9,636,442 B2 5/2017 Karmon et al.
9,669,144 B2 6/2017 Spanier et al.
9,675,738 B2 6/2017 Tanner et al.
9,675,739 B2 6/2017 Tanner et al.
9,675,740 B2 6/2017 Zeng et al.
9,682,180 B2 6/2017 Hoarau et al.
9,717,833 B2 8/2017 McBride et al.
9,731,058 B2 8/2017 Siebenhaar et al.
9,759,222 B2 9/2017 Zimmermann et al.
9,770,543 B2 9/2017 Tanner et al.
9,789,238 B2 10/2017 Aboul-Hosn et al.
9,801,990 B2 10/2017 Lynch
9,814,813 B2 11/2017 Corbett
9,821,100 B2 11/2017 Corbett et al.
9,833,550 B2 12/2017 Siess
9,849,223 B2 12/2017 LaRose
9,872,948 B2 1/2018 Siess
9,878,087 B2 1/2018 Richardson et al.
9,907,890 B2 3/2018 Muller
9,919,087 B2 3/2018 Pfeffer et al.
9,950,101 B2 4/2018 Smith et al.
9,968,719 B2 5/2018 Colella
9,999,714 B2 6/2018 Spanier et al.
10,029,037 B2 7/2018 Muller et al.
10,123,875 B2 11/2018 Wildhirt et al.
10,124,102 B2 11/2018 Bulent et al.
10,130,742 B2 11/2018 Tuseth
10,149,932 B2 12/2018 McBride et al.
10,179,197 B2 1/2019 Kaiser et al.
10,201,645 B2 2/2019 Muller
10,207,038 B2 2/2019 Neumann
10,220,129 B2 3/2019 Ayre et al.
10,232,099 B2 3/2019 Peters et al.
10,238,782 B2 3/2019 Barry
10,238,783 B2 3/2019 Aboul-Hosn et al.
10,251,986 B2 4/2019 Larose et al.
10,279,093 B2 5/2019 Reichenbach et al.
10,293,090 B2 5/2019 Bonde et al.
10,300,185 B2 5/2019 Aboul-Hosn et al.
10,300,249 B2 5/2019 Tao et al.
10,322,217 B2 6/2019 Spence
10,342,906 B2 7/2019 D'Ambrosio et al.
10,357,598 B2 7/2019 Aboul-Hosn et al.
10,361,617 B2 7/2019 Mueller et al.
10,371,150 B2 8/2019 Wu et al.
10,376,162 B2 8/2019 Edelman et al.
10,420,869 B2 9/2019 Cornen
10,434,232 B2 10/2019 Wu et al.

(56) References Cited

U.S. PATENT DOCUMENTS 10,449,275 B2 10/2019 Corbett
10,449,279 B2 10/2019 Muller
10,478,538 B2 11/2019 Scheckel et al.
10,478,539 B2 11/2019 Pfeffer et al.
10,478,542 B2 11/2019 Jahangir
10,500,323 B2 12/2019 Heuring et al.
10,512,537 B2 12/2019 Corbett et al.
10,525,178 B2 1/2020 Zeng
10,537,670 B2 1/2020 Tuseth et al.
10,537,672 B2 1/2020 Tuseth et al.
10,557,475 B2 2/2020 Roehn
10,561,771 B2 2/2020 Heilman et al.
10,561,772 B2 2/2020 Schumacher
10,576,191 B2 3/2020 LaRose
10,584,589 B2 3/2020 Schumacher et al.
10,589,012 B2 3/2020 Toellner et al.
10,589,013 B2 3/2020 Bourque
10,610,626 B2 4/2020 Spanier et al.
10,617,808 B2 4/2020 Hastie et al.
10,632,241 B2 4/2020 Schenck et al.
10,660,998 B2 5/2020 Hodges
10,662,967 B2 5/2020 Scheckel
10,668,195 B2 6/2020 Flores
10,669,855 B2 6/2020 Toellner et al.
10,722,631 B2 7/2020 Salahieh et al.
10,773,002 B2 9/2020 Siess et al.
10,780,208 B2 9/2020 Siess et al.
10,814,053 B2 10/2020 Throckmorton et al.
10,857,273 B2 12/2020 Hodges et al.
10,857,274 B2 12/2020 Alexander et al.
10,864,308 B2 12/2020 Muller et al.
11,027,114 B2 6/2021 D'Ambrosio et al.
11,033,729 B2 6/2021 Scheckel et al.
11,045,638 B2 6/2021 Keenan et al.
11,058,863 B2 7/2021 Demou
11,058,865 B2 7/2021 Fitzgerald et al.
11,065,434 B2 7/2021 Egler et al.
11,092,158 B2 8/2021 Siess et al.
11,097,092 B2 8/2021 Siess et al.
11,103,689 B2 8/2021 Siess et al.
11,103,690 B2 8/2021 Epple
11,107,626 B2 8/2021 Siess et al.
11,116,959 B2 9/2021 Alexander et al.
11,123,538 B2 9/2021 Epple et al.
11,123,539 B2 9/2021 Pfeffer et al.
11,123,541 B2 9/2021 Corbett et al.
11,129,978 B2 9/2021 Pfeffer et al.
11,141,579 B2 10/2021 Steingräber
11,160,970 B2 11/2021 Muller et al.
11,167,124 B2 11/2021 Pfeffer et al.
11,173,297 B2 11/2021 Muller
11,179,557 B2 11/2021 Georges et al.
11,185,678 B2 11/2021 Smith et al.
11,185,680 B2 11/2021 Tuval et al.
11,191,944 B2 12/2021 Tuval et al.
11,197,989 B2 12/2021 Arslan et al.
11,202,901 B2 12/2021 Barry
11,219,756 B2 1/2022 Tanner et al.
11,229,786 B2 1/2022 Zeng et al.
11,235,138 B2 2/2022 Gross-Hardt et al.
11,235,140 B2 2/2022 Siess et al.
11,241,568 B2 2/2022 Keenan et al.
11,241,569 B2 2/2022 Delgado, III
11,253,693 B2 2/2022 Pfeffer et al.
11,260,212 B2 3/2022 Tuval et al.
11,260,213 B2 3/2022 Zeng et al.
11,260,215 B2 3/2022 Scheckel et al.
11,273,300 B2 3/2022 Schafir
11,273,301 B2 3/2022 Pfeffer et al.
11,278,711 B2 3/2022 Liebing
11,280,345 B2 3/2022 Bredenbreuker et al.
11,285,309 B2 3/2022 Tuval et al.
11,291,824 B2 4/2022 Schwammenthal et al.
11,291,825 B2 4/2022 Tuval et al.
11,291,826 B2 4/2022 Tuval et al.
11,298,519 B2 4/2022 Josephy et al.
11,298,520 B2 4/2022 Schwammenthal et al.
11,298,521 B2 4/2022 Schwammenthal et al.
11,298,523 B2 4/2022 Tuval et al.
11,298,524 B2 4/2022 El Katerji et al.
11,298,525 B2 4/2022 Jahangir
11,305,103 B2 4/2022 Larose et al.
11,305,105 B2 4/2022 Corbett et al.
11,311,711 B2 4/2022 Casas et al.
11,311,712 B2 4/2022 Zeng et al.
11,313,228 B2 4/2022 Schumacher et al.
D951,435 S 5/2022 Motomura et al.
11,318,295 B2 5/2022 Reyes et al.
11,324,940 B2 5/2022 Earles et al.
11,324,941 B2 5/2022 Xu et al.
11,331,465 B2 5/2022 Epple
11,331,466 B2 5/2022 Keen et al.
11,331,467 B2 5/2022 King et al.
11,331,470 B2 5/2022 Muller et al.
11,338,124 B2 5/2022 Pfeffer et al.
11,338,125 B2 5/2022 Liu et al.
11,344,716 B2 5/2022 Taskin
11,344,717 B2 5/2022 Kallenbach et al.
11,351,356 B2 6/2022 Mohl
11,351,357 B2 6/2022 Mohl
11,351,359 B2 6/2022 Clifton et al.
11,357,967 B2 6/2022 Zeng et al.
11,364,373 B2 6/2022 Corbett et al.
11,368,081 B2 6/2022 Vogt et al.
11,369,785 B2 6/2022 Callaway et al.
11,369,786 B2 6/2022 Menon et al.
11,376,415 B2 7/2022 Mohl
11,389,639 B2 7/2022 Casas
11,389,641 B2 7/2022 Nguyen et al.
11,413,443 B2 8/2022 Hodges et al.
11,413,446 B2 8/2022 Siess et al.
11,415,150 B2 8/2022 Richert et al.
11,421,701 B2 8/2022 Schumacher et al.
11,428,236 B2 8/2022 McBride et al.
11,433,168 B2 9/2022 Wu et al.
11,434,921 B2 9/2022 McBride et al.
11,434,922 B2 9/2022 Roehn
11,446,481 B2 9/2022 Wolman et al.
11,446,482 B2 9/2022 Kirchhoff et al.
11,452,859 B2 9/2022 Earles et al.
11,460,030 B2 10/2022 Shambaugh et al.
11,471,662 B2 10/2022 Akkerman et al.
11,471,663 B2 10/2022 Tuval et al.
11,471,665 B2 10/2022 Clifton et al.
11,478,627 B2 10/2022 Siess et al.
11,478,628 B2 10/2022 Muller et al.
11,478,629 B2 10/2022 Harjes et al.
11,484,698 B2 11/2022 Radman
11,484,699 B2 11/2022 Tuval et al.
11,486,400 B2 11/2022 Schumacher
11,491,320 B2 11/2022 Siess
11,491,322 B2 11/2022 Muller et al.
11,497,896 B2 11/2022 Tanner et al.
11,497,906 B2 11/2022 Grace et al.
11,511,101 B2 11/2022 Hastie et al.
11,511,103 B2 11/2022 Salahieh et al.
11,511,104 B2 11/2022 Dur et al.
11,517,726 B2 12/2022 Siess et al.
11,517,736 B2 12/2022 Earles et al.
11,517,737 B2 12/2022 Struthers et al.
11,517,738 B2 12/2022 Wisniewski
11,517,739 B2 12/2022 Toellner
11,517,740 B2 12/2022 Agarwa et al.
11,524,137 B2 12/2022 Jahangir
11,524,153 B2 12/2022 Alexander et al.
11,524,165 B2 12/2022 Tan et al.
11,529,062 B2 12/2022 Moyer et al.
11,534,596 B2 12/2022 Schafir et al.
11,565,103 B2 1/2023 Farago et al.
11,569,015 B2 1/2023 Mourran et al.
11,572,879 B2 2/2023 Mohl
11,577,067 B2 2/2023 Breidall et al.
11,577,068 B2 2/2023 Spence et al.
11,583,659 B2 2/2023 Pfeffer et al.

(56) References Cited

U.S. PATENT DOCUMENTS 11,583,670 B2 2/2023 Pfeifer et al.
11,583,671 B2 2/2023 Nguyen et al.
11,583,672 B2 2/2023 Weber et al.
11,590,336 B2 2/2023 Harjes et al.
11,590,337 B2 2/2023 Granegger et al.
11,590,338 B2 2/2023 Barry
11,592,028 B2 2/2023 Schumacher et al.
11,596,727 B2 3/2023 Siess et al.
11,602,627 B2 3/2023 Leonhardt
11,617,876 B2 4/2023 Scheckel et al.
11,628,293 B2 4/2023 Gandhi et al.
11,632,015 B2 4/2023 Sconzert et al.
11,633,586 B2 4/2023 Tanner et al.
11,638,813 B2 5/2023 West
11,639,722 B2 5/2023 Medvedev et al.
11,642,511 B2 5/2023 Delgado, III
11,648,387 B2 5/2023 Schwammenthal et al.
11,648,388 B2 5/2023 Siess et al.
11,648,389 B2 5/2023 Wang et al.
11,648,390 B2 5/2023 Spanier et al.
11,648,391 B2 5/2023 Schwammenthal et al.
11,648,392 B2 5/2023 Tuval et al.
11,648,393 B2 5/2023 Taskin et al.
11,654,273 B2 5/2023 Granegger et al.
11,654,275 B2 5/2023 Brandt
11,654,276 B2 5/2023 Fitzgerald et al.
11,660,441 B2 5/2023 Fitzgerald et al.
11,666,747 B2 6/2023 Tuval et al.
11,666,748 B2 6/2023 Kronstedt et al.
11,668,321 B2 6/2023 Richert et al.
11,674,517 B2 6/2023 Mohl
11,679,234 B2 6/2023 King et al.
11,679,249 B2 6/2023 Scheckel et al.
11,679,250 B2 6/2023 Alexander et al.
11,684,275 B2 6/2023 Tuval et al.
11,684,769 B2 6/2023 Harjes et al.
11,690,521 B2 7/2023 Tuval et al.
11,690,996 B2 7/2023 Siess et al.
11,697,016 B2 7/2023 Epple
11,701,510 B2 7/2023 Demou
11,702,938 B2 7/2023 Schumacher et al.
11,703,064 B2 7/2023 Bredenbreuker et al.
11,708,833 B2 7/2023 McBride et al.
11,744,987 B2 9/2023 Siess et al.
11,745,005 B2 9/2023 Delgado, III
11,746,906 B1 9/2023 Balta et al.
11,752,322 B2 9/2023 Aboulhosn et al.
11,752,323 B2 9/2023 Edwards et al.
11,754,075 B2 9/2023 Schuelke et al.
11,754,077 B1 9/2023 Mohl
11,759,612 B2 9/2023 Tanner et al.
11,759,622 B2 9/2023 Siess et al.
11,766,555 B2 9/2023 Matthes et al.
11,771,884 B2 10/2023 Siess et al.
11,771,885 B2 10/2023 Liu et al.
11,779,234 B2 10/2023 Harjes et al.
11,779,751 B2 10/2023 Earles et al.
11,781,551 B2 10/2023 Yanai et al.
11,786,386 B2 10/2023 Brady et al.
11,786,700 B2 10/2023 Pfeffer et al.
11,786,720 B2 10/2023 Muller
11,793,994 B2 10/2023 Josephy et al.
11,804,767 B2 10/2023 Vogt et al.
11,806,116 B2 11/2023 Tuval et al.
11,806,117 B2 11/2023 Tuval et al.
11,806,517 B2 11/2023 Petersen
11,806,518 B2 11/2023 Michelena et al.
11,813,443 B2 11/2023 Hanson et al.
11,813,444 B2 11/2023 Siess et al.
11,813,445 B2 11/2023 Alexander et al.
11,819,678 B2 11/2023 Siess et al.
11,826,127 B2 11/2023 Casas
11,833,278 B2 12/2023 Siess et al.
11,833,342 B2 12/2023 Tanner et al.
11,839,754 B2 12/2023 Tuval et al.
11,844,592 B2 12/2023 Tuval et al.
11,844,940 B2 12/2023 D'Ambrosio et al.
11,850,412 B2 12/2023 Grauwinkel et al.
11,850,413 B2 12/2023 Zeng et al.
11,850,414 B2 12/2023 Schenck et al.
11,850,415 B2 12/2023 Schwammenthal et al.
11,857,743 B2 1/2024 Fantuzzi et al.
11,857,777 B2 1/2024 Earles et al.
11,865,238 B2 1/2024 Siess et al.
11,872,384 B2 1/2024 Cotter
11,883,005 B2 1/2024 Golden et al.
11,883,207 B2 1/2024 El Katerji et al.
11,883,310 B2 1/2024 Nolan et al.
11,883,641 B2 1/2024 Dur et al.
11,890,212 B2 2/2024 Gilmartin et al.
11,896,482 B2 2/2024 Delaloye et al.
11,898,642 B2 2/2024 Stanton et al.
11,904,104 B2 2/2024 Jahangir
11,911,579 B2 2/2024 Tanner et al.
11,918,470 B2 3/2024 Jarral et al.
11,918,496 B2 3/2024 Folan
11,918,726 B2 3/2024 Siess et al.
11,918,800 B2 3/2024 Muller et al.
11,925,356 B2 3/2024 Anderson et al.
11,925,570 B2 3/2024 Lydecker et al.
11,925,794 B2 3/2024 Malkin et al.
11,925,795 B2 3/2024 Muller et al.
11,925,796 B2 3/2024 Tanner et al.
11,925,797 B2 3/2024 Tanner et al.
11,938,311 B2 3/2024 Corbett et al.
11,944,805 B2 4/2024 Stotz
11,957,892 B2 4/2024 Siess et al.
11,980,385 B2 5/2024 Haselman
11,986,604 B2 5/2024 Siess
12,005,248 B2 6/2024 Vogt et al.
12,011,583 B2 6/2024 Wang
12,017,058 B2 6/2024 Kerkhoffs et al.
12,023,476 B2 7/2024 Tuval et al.
12,023,477 B2 7/2024 Siess
12,053,624 B2 8/2024 Alexander et al.
12,059,559 B2 8/2024 Muller et al.
12,064,120 B2 8/2024 Hajjar et al.
12,064,611 B2 8/2024 D'Ambrosio et al.
12,064,614 B2 8/2024 Agah et al.
12,064,615 B2 8/2024 Stotz et al.
12,064,616 B2 8/2024 Spanier et al.
12,076,544 B2 9/2024 Siess et al.
12,076,549 B2 9/2024 Stotz et al.
12,076,550 B2 9/2024 Edwards et al.
12,090,310 B2 9/2024 Alexander et al.
12,090,314 B2 9/2024 Tuval et al.
12,092,114 B2 9/2024 Siess
12,097,016 B2 9/2024 Goldvasser
12,102,815 B2 10/2024 Dhaliwal et al.
12,104,600 B2 10/2024 Mohl
12,107,474 B2 10/2024 Vollmer
12,117,007 B1 10/2024 Mohl
12,121,713 B2 10/2024 Calomeni et al.
12,133,976 B2 11/2024 Malone et al.
12,138,438 B2 11/2024 Alexander et al.
12,144,936 B2 11/2024 Tao et al.
12,144,976 B2 11/2024 Baumbach et al.
12,151,092 B2 11/2024 Alexander et al.
12,161,854 B2 12/2024 Earles et al.
12,161,855 B2 12/2024 Hastie et al.
12,161,857 B2 12/2024 Saul et al.
12,171,993 B2 12/2024 Higgins et al.
12,194,287 B2 1/2025 Kassel et al.
12,196,210 B2 1/2025 Siess et al.
12,201,823 B2 1/2025 Baumbach et al.
12,207,906 B2 1/2025 Tuval et al.
12,213,771 B2 2/2025 Curran et al.
12,233,251 B2 2/2025 Siess et al.
12,241,480 B2 3/2025 Corbett et al.
12,263,330 B2 4/2025 D'Ambrosio et al.
12,263,333 B2 4/2025 Stotz et al.
12,263,334 B2 4/2025 Corbett et al.
12,268,861 B2 4/2025 D'Ambrosio et al.
12,290,673 B2 5/2025 Jahangir

(56) References Cited

U.S. PATENT DOCUMENTS 12,290,676 B2 5/2025 Farago et al.
12,303,678 B2 5/2025 Kerkhoffs et al.
12,303,680 B2 5/2025 Siess et al.
12,318,551 B2 6/2025 Jahangir
12,329,958 B2 6/2025 Siess et al.
12,337,163 B2 6/2025 Radman
12,343,516 B2 7/2025 Cook
12,343,518 B2 7/2025 Tuval et al.
12,343,519 B2 7/2025 Siess et al.
12,364,799 B2 7/2025 Siess et al.
12,364,850 B2 7/2025 Siess et al.
12,364,854 B2 7/2025 Wang
12,383,704 B2 8/2025 Ship et al.
12,383,724 B2 8/2025 Kirchoff et al.
12,383,727 B2 8/2025 Kassel et al.
12,390,633 B2 8/2025 Stotz et al.
12,397,146 B2 8/2025 Hart et al.
D1,092,716 S 9/2025 Bernazani
12,409,311 B2 9/2025 Jahangir et al.
12,415,056 B2 9/2025 Siess et al.
12,420,076 B2 9/2025 Spanier et al.
12,420,079 B2 9/2025 Das et al.
12,434,060 B2 10/2025 Tan et al.
12,440,663 B2 10/2025 Tuval et al.
12,440,665 B2 10/2025 Tuval et al.
12,447,309 B2 10/2025 Siess et al.
12,447,327 B2 10/2025 Stotz
12,453,847 B2 10/2025 Scheffler et al.
12,453,848 B2 10/2025 Tuval et al.
12,453,849 B2 10/2025 Vancamp et al.
D1,101,157 S 11/2025 Qi et al.
12,458,792 B2 11/2025 Zarins
12,465,744 B2 11/2025 Schuelke et al.
12,465,748 B2 11/2025 Calomeni et al.
12,478,774 B2 11/2025 Muller
12,478,775 B2 11/2025 Schlebusch et al.
12,478,776 B2 11/2025 Stotz
12,491,062 B2 12/2025 Schwammenthal et al.
12,494,292 B2 12/2025 El Katerji et al.
12,502,521 B2 12/2025 Siess et al.
12,515,036 B2 1/2026 Bette et al.
12,515,038 B2 1/2026 Weber et al.
12,521,546 B2 1/2026 Siess et al.
12,523,228 B2 1/2026 Schuelke et al.
2001/0009645 A1 7/2001 Noda
2001/0041934 A1 11/2001 Yamazaki et al.
2002/0076322 A1 6/2002 Maeda et al.
2002/0082585 A1 6/2002 Carroll et al.
2002/0147495 A1 10/2002 Petroff
2002/0153664 A1 10/2002 Schroeder
2003/0060685 A1 3/2003 Houser
2003/0091450 A1 5/2003 Davis et al.
2003/0100816 A1 5/2003 Siess
2003/0111800 A1 6/2003 Kreutzer
2003/0139643 A1 7/2003 Smith et al.
2003/0191357 A1 10/2003 Frazier
2003/0199727 A1 10/2003 Burke
2004/0044266 A1 3/2004 Siess et al.
2004/0066107 A1 4/2004 Gery
2004/0102674 A1 5/2004 Zadini et al.
2004/0115038 A1 6/2004 Nuesser et al.
2004/0167376 A1 8/2004 Peters et al.
2004/0234391 A1 11/2004 Izraelev
2004/0241019 A1 12/2004 Goldowsky
2004/0260346 A1 12/2004 Overall et al.
2005/0006083 A1 1/2005 Chen et al.
2005/0008509 A1 1/2005 Chang
2005/0019167 A1 1/2005 Nusser et al.
2005/0085683 A1 4/2005 Bolling et al.
2005/0220636 A1 10/2005 Henein et al.
2005/0254976 A1 11/2005 Carrier et al.
2006/0030809 A1 2/2006 Barzilay et al.
2006/0062672 A1 3/2006 McBride et al.
2006/0155158 A1 7/2006 Aboul-Hosn
2006/0224110 A1 10/2006 Scott et al.
2006/0276682 A1 12/2006 Bolling et al.
2007/0004959 A1 1/2007 Carrier et al.
2007/0142696 A1 6/2007 Crosby et al.
2007/0156006 A1 7/2007 Smith et al.
2008/0015517 A1 1/2008 Geistert et al.
2008/0058925 A1 3/2008 Cohen
2008/0086027 A1 4/2008 Siess et al.
2008/0114339 A1 5/2008 McBride et al.
2008/0262289 A1 10/2008 Goldowsky
2008/0292478 A1 11/2008 Baykut et al.
2008/0306328 A1 12/2008 Ercolani
2009/0004037 A1 1/2009 Ito
2009/0112312 A1 4/2009 Larose et al.
2009/0138080 A1 5/2009 Siess et al.
2009/0203957 A1 8/2009 LaRose et al.
2009/0204205 A1 8/2009 Larose et al.
2010/0041939 A1 2/2010 Siess
2010/0082099 A1 4/2010 Vodermayer et al.
2010/0191035 A1 7/2010 Kang et al.
2010/0268017 A1 10/2010 Siess
2010/0298625 A1 11/2010 Reichenbach et al.
2011/0172505 A1 7/2011 Kim
2011/0184224 A1 7/2011 Garrigue
2011/0230821 A1 9/2011 Babic
2011/0237863 A1 9/2011 Ricci et al.
2011/0238172 A1 9/2011 Akdis
2012/0029265 A1 2/2012 LaRose
2012/0035645 A1 2/2012 Gross
2012/0088954 A1 4/2012 Foster
2012/0093628 A1 4/2012 Liebing
2012/0134793 A1 5/2012 Wu et al.
2012/0172655 A1 7/2012 Campbell et al.
2012/0178986 A1 7/2012 Campbell et al.
2012/0245404 A1 9/2012 Smith
2012/0247200 A1 10/2012 Ahonen et al.
2012/0283506 A1 11/2012 Meister et al.
2012/0310036 A1 12/2012 Peters et al.
2013/0053623 A1 2/2013 Evans
2013/0085318 A1 4/2013 Toellner
2013/0209292 A1 8/2013 Baykut et al.
2013/0281761 A1 10/2013 Kapur
2013/0289376 A1 10/2013 Lang
2013/0303830 A1 11/2013 Zeng et al.
2013/0303831 A1 11/2013 Evans
2013/0303832 A1 11/2013 Wampler
2013/0330219 A1 12/2013 LaRose et al.
2014/0005467 A1 1/2014 Farnan et al.
2014/0030122 A1 1/2014 Ozaki
2014/0051908 A1 2/2014 Khanal et al.
2014/0079557 A1 3/2014 LaRose et al.
2014/0107399 A1 4/2014 Spence
2014/0167545 A1 6/2014 Bremner et al.
2014/0194717 A1 7/2014 Wildhirt et al.
2014/0200389 A1 7/2014 Yanai et al.
2014/0207232 A1 7/2014 Garrigue
2014/0275721 A1 9/2014 Yanai et al.
2014/0330069 A1 11/2014 Hastings et al.
2014/0341726 A1 11/2014 Wu et al.
2014/0368942 A1 12/2014 Harrell
2015/0031936 A1 1/2015 LaRose et al.
2015/0051435 A1 2/2015 Siess et al.
2015/0051438 A1 2/2015 Taskin
2015/0080743 A1 3/2015 Siess
2015/0099923 A1 4/2015 Magovern et al.
2015/0141842 A1 5/2015 Spanier et al.
2015/0171694 A1 6/2015 Dallas
2015/0190092 A1 7/2015 Mori
2015/0273184 A1 10/2015 Scott et al.
2015/0290372 A1 10/2015 Muller et al.
2015/0290373 A1 10/2015 Rudser et al.
2015/0306291 A1 10/2015 Bonde et al.
2015/0343179 A1 12/2015 Schumacher et al.
2015/0362017 A1* 12/2015 Bell .................... F16C 33/1095 384/300
2015/0365738 A1 12/2015 Purvis et al.
2016/0008531 A1 1/2016 Wang et al.
2016/0030649 A1 2/2016 Zeng
2016/0038663 A1 2/2016 Taskin et al.
2016/0045654 A1 2/2016 Connor

(56) References Cited

U.S. PATENT DOCUMENTS

2016/0067395 A1 3/2016 Jimenez et al.
2016/0101224 A1 4/2016 Akkerman
2016/0144089 A1 5/2016 Woo et al.
2016/0144166 A1 5/2016 Decré et al.
2016/0166747 A1 6/2016 Frazier et al.
2016/0184499 A1 6/2016 Ricci
2016/0213828 A1 7/2016 Sievers
2016/0223086 A1 8/2016 Balsells et al.
2016/0256620 A1 9/2016 Scheckel et al.
2016/0279311 A1 9/2016 Cecere et al.
2016/0367739 A1 12/2016 Wiesener et al.
2016/0375187 A1 12/2016 Lee et al.
2017/0021069 A1 1/2017 Hodges
2017/0021074 A1 1/2017 Opfermann et al.
2017/0035952 A1 2/2017 Muller
2017/0043074 A1 2/2017 Siess
2017/0049947 A1 2/2017 Corbett et al.
2017/0080136 A1 3/2017 Janeczek et al.
2017/0087286 A1 3/2017 Spanier et al.
2017/0087288 A1 3/2017 Groß-Hardt et al.
2017/0128644 A1 5/2017 Foster
2017/0136225 A1 5/2017 Siess et al.
2017/0143952 A1 5/2017 Siess et al.
2017/0157309 A1 6/2017 Begg et al.
2017/0209633 A1 7/2017 Cohen
2017/0232169 A1 8/2017 Muller
2017/0274128 A1 9/2017 Tamburino et al.
2017/0317573 A1 11/2017 Mueller et al.
2017/0333607 A1 11/2017 Zarins
2017/0333608 A1 11/2017 Zeng
2017/0340787 A1 11/2017 Corbett et al.
2017/0340788 A1 11/2017 Korakianitis et al.
2017/0340789 A1 11/2017 Bonde et al.
2017/0343043 A1 11/2017 Walsh et al.
2018/0015214 A1 1/2018 Lynch
2018/0021494 A1 1/2018 Muller et al.
2018/0021495 A1 1/2018 Muller et al.
2018/0050141 A1 2/2018 Corbett et al.
2018/0055979 A1 3/2018 Corbett et al.
2018/0064860 A1 3/2018 Nunez et al.
2018/0093070 A1 4/2018 Cottone
2018/0099076 A1 4/2018 LaRose
2018/0110907 A1 4/2018 Keenan et al.
2018/0133379 A1 5/2018 Farnan et al.
2018/0154058 A1 6/2018 Menon et al.
2018/0169312 A1 6/2018 Barry
2018/0169313 A1 6/2018 Schwammenthal et al.
2018/0207336 A1 7/2018 Solem
2018/0219452 A1 8/2018 Boisclair
2018/0221551 A1 8/2018 Tanner et al.
2018/0221553 A1 8/2018 Taskin
2018/0228950 A1 8/2018 Janeczek et al.
2018/0228953 A1 8/2018 Siess et al.
2018/0243004 A1 8/2018 von Segesser et al.
2018/0243489 A1 8/2018 Haddadi
2018/0250456 A1 9/2018 Nitzan et al.
2018/0256797 A1 9/2018 Schenck et al.
2018/0280598 A1 10/2018 Curran et al.
2018/0289877 A1 10/2018 Schumacher et al.
2018/0303990 A1 10/2018 Siess et al.
2018/0303991 A1 10/2018 Nüsser et al.
2018/0311421 A1 11/2018 Tuseth
2018/0311423 A1 11/2018 Zeng et al.
2018/0318483 A1 11/2018 Dague et al.
2018/0318547 A1 11/2018 Yokoyama
2018/0326132 A1 11/2018 Maimon et al.
2018/0333059 A1 11/2018 Casas
2018/0335037 A1 11/2018 Shambaugh et al.
2018/0345028 A1 12/2018 Aboud et al.
2018/0361042 A1 12/2018 Fitzgerald et al.
2018/0369469 A1 12/2018 Le Duc De Lillers et al.
2019/0001034 A1 1/2019 Taskin et al.
2019/0004037 A1 1/2019 Zhang et al.
2019/0030228 A1 1/2019 Keenan et al.
2019/0046702 A1 2/2019 Siess et al.
2019/0046703 A1 2/2019 Shambaugh et al.
2019/0054223 A1 2/2019 Frazier et al.
2019/0060539 A1 2/2019 Siess et al.
2019/0060543 A1 2/2019 Khanal et al.
2019/0076167 A1 3/2019 Fantuzzi et al.
2019/0083690 A1 3/2019 Siess et al.
2019/0099532 A1 4/2019 Er
2019/0101130 A1 4/2019 Bredenbreuker et al.
2019/0105437 A1 4/2019 Siess et al.
2019/0117865 A1 4/2019 Walters et al.
2019/0125948 A1 5/2019 Stanfield et al.
2019/0143016 A1 5/2019 Corbett et al.
2019/0143018 A1 5/2019 Salahieh et al.
2019/0154053 A1 5/2019 McBride et al.
2019/0167122 A1 6/2019 Obermiller et al.
2019/0167875 A1 6/2019 Simon et al.
2019/0167878 A1 6/2019 Rowe
2019/0170153 A1 6/2019 Scheckel
2019/0175806 A1 6/2019 Tuval et al.
2019/0184078 A1 6/2019 Zilbershlag et al.
2019/0184080 A1 6/2019 Mohl
2019/0192752 A1 6/2019 Tiller et al.
2019/0199165 A1 6/2019 Carson
2019/0201603 A1 7/2019 Siess et al.
2019/0209755 A1 7/2019 Nix et al.
2019/0209758 A1 7/2019 Tuval et al.
2019/0211836 A1 7/2019 Schumacher et al.
2019/0211846 A1 7/2019 Liebing
2019/0211847 A1 7/2019 Walsh et al.
2019/0223877 A1 7/2019 Nitzen et al.
2019/0269840 A1 9/2019 Tuval et al.
2019/0275224 A1 9/2019 Hanson et al.
2019/0282741 A1 9/2019 Franano et al.
2019/0282744 A1 9/2019 D'Ambrosio et al.
2019/0282746 A1 9/2019 Judisch
2019/0290817 A1 9/2019 Guo et al.
2019/0298902 A1 10/2019 Siess et al.
2019/0316591 A1 10/2019 Toellner
2019/0321527 A1 10/2019 King et al.
2019/0321529 A1 10/2019 Korakianitis et al.
2019/0321531 A1 10/2019 Cambronne et al.
2019/0336664 A1 11/2019 Liebing
2019/0344000 A1 11/2019 Kushwaha et al.
2019/0344001 A1 11/2019 Salahieh et al.
2019/0351117 A1 11/2019 Cambronne et al.
2019/0351119 A1 11/2019 Cambronne et al.
2019/0351120 A1 11/2019 Kushwaha et al.
2019/0358378 A1 11/2019 Schumacher
2019/0358379 A1 11/2019 Wiessler et al.
2019/0358384 A1 11/2019 Epple
2019/0365975 A1 12/2019 Muller et al.
2019/0383298 A1 12/2019 Toellner
2020/0016309 A1 1/2020 Kallenbach et al.
2020/0023109 A1 1/2020 Epple
2020/0030507 A1 1/2020 Higgins et al.
2020/0030509 A1 1/2020 Siess et al.
2020/0030510 A1 1/2020 Higgins
2020/0030511 A1 1/2020 Higgins
2020/0030512 A1 1/2020 Higgins et al.
2020/0038567 A1 2/2020 Siess et al.
2020/0038568 A1 2/2020 Higgins et al.
2020/0038571 A1 2/2020 Jahangir
2020/0069857 A1 3/2020 Schwammenthal et al.
2020/0088207 A1 3/2020 Schumacher et al.
2020/0114053 A1 4/2020 Salahieh et al.
2020/0129684 A1 4/2020 Pfeffer et al.
2020/0139028 A1 5/2020 Scheckel et al.
2020/0139029 A1 5/2020 Scheckel et al.
2020/0147283 A1 5/2020 Tanner et al.
2020/0164125 A1 5/2020 Muller et al.
2020/0164126 A1 5/2020 Muller
2020/0261633 A1 8/2020 Spanier
2020/0345337 A1 11/2020 Muller et al.
2020/0350812 A1 11/2020 Vogt et al.
2021/0052793 A1 2/2021 Struthers et al.
2021/0236803 A1 8/2021 Stotz
2021/0268264 A1 9/2021 Stotz
2021/0290929 A1 9/2021 Stotz
2021/0290930 A1 9/2021 Kasel

(56) References Cited

U.S. PATENT DOCUMENTS

| | | | |
|---|---|---|---|
| 2021/0290932 | A1 | 9/2021 | Stotz |
| 2021/0290937 | A1 | 9/2021 | Baumbach |
| 2021/0313869 | A1 | 10/2021 | Strasswiemer et al. |
| 2021/0316133 | A1 | 10/2021 | Kassel et al. |
| 2021/0322756 | A1 | 10/2021 | Vollmer et al. |
| 2021/0330958 | A1 | 10/2021 | Stotz et al. |
| 2021/0338999 | A1 | 11/2021 | Stotz et al. |
| 2021/0339004 | A1 | 11/2021 | Schlebusch et al. |
| 2021/0339005 | A1 | 11/2021 | Stotz et al. |
| 2021/0346678 | A1 | 11/2021 | Baumbach et al. |
| 2021/0346680 | A1 | 11/2021 | Vogt et al. |
| 2021/0379352 | A1 | 12/2021 | Schlebusch et al. |
| 2021/0379355 | A1 | 12/2021 | Schuelke et al. |
| 2021/0384812 | A1 | 12/2021 | Vollmer et al. |
| 2022/0008714 | A1 | 1/2022 | Stotz |
| 2022/0016411 | A1 | 1/2022 | Winterwerber |
| 2022/0072296 | A1 | 3/2022 | Mori |
| 2022/0072297 | A1 | 3/2022 | Tuval et al. |
| 2022/0080178 | A1 | 3/2022 | Salahieh et al. |
| 2022/0080180 | A1 | 3/2022 | Siess et al. |
| 2022/0080182 | A1 | 3/2022 | Earles et al. |
| 2022/0080183 | A1 | 3/2022 | Earles et al. |
| 2022/0080184 | A1 | 3/2022 | Clifton et al. |
| 2022/0080185 | A1 | 3/2022 | Clifton et al. |
| 2022/0105337 | A1 | 4/2022 | Salahieh et al. |
| 2022/0105339 | A1 | 4/2022 | Nix et al. |
| 2022/0126083 | A1 | 4/2022 | Grauwinkel et al. |
| 2022/0161018 | A1 | 5/2022 | Mitze et al. |
| 2022/0161019 | A1 | 5/2022 | Mitze et al. |
| 2022/0161021 | A1 | 5/2022 | Mitze et al. |
| 2022/0249829 | A1 | 8/2022 | Edwards et al. |
| 2022/0323742 | A1 | 10/2022 | Grauwinkel et al. |
| 2023/0001178 | A1 | 1/2023 | Corbett et al. |
| 2023/0063798 | A1 | 3/2023 | Edwards et al. |
| 2023/0079625 | A1 | 3/2023 | Theran et al. |
| 2023/0105131 | A1 | 4/2023 | Kerkhoffs et al. |
| 2023/0125439 | A1 | 4/2023 | Malone et al. |
| 2023/0128328 | A1 | 4/2023 | Malone et al. |
| 2023/0130285 | A1 | 4/2023 | Malone et al. |
| 2023/0149691 | A1 | 5/2023 | VanCamp et al. |
| 2023/0149692 | A1 | 5/2023 | Larsen et al. |
| 2023/0158289 | A1 | 5/2023 | Breidall et al. |
| 2023/0233834 | A1 | 7/2023 | Alexander et al. |
| 2023/0277833 | A1 | 9/2023 | Sharma et al. |
| 2023/0277836 | A1 | 9/2023 | Schellenberg et al. |
| 2023/0293878 | A1 | 9/2023 | Christof et al. |
| 2023/0364411 | A1 | 11/2023 | Bette |
| 2023/0381492 | A1 | 11/2023 | Alexander et al. |
| 2024/0075277 | A1 | 3/2024 | Schellenberg |
| 2024/0102475 | A1 | 3/2024 | Schuelke et al. |
| 2024/0198084 | A1 | 6/2024 | Stotz |
| 2024/0245902 | A1 | 7/2024 | Schlebusch et al. |
| 2024/0269459 | A1 | 8/2024 | Schellenberg et al. |
| 2024/0277998 | A1 | 8/2024 | Vogt et al. |
| 2024/0285935 | A1 | 8/2024 | Popov et al. |
| 2024/0335651 | A1 | 10/2024 | Mitze et al. |
| 2024/0399135 | A1 | 12/2024 | Stotz et al. |
| 2025/0032773 | A1 | 1/2025 | Baumbach et al. |
| 2025/0121177 | A1 | 4/2025 | West |
| 2025/0144397 | A1 | 5/2025 | Kassel et al. |
| 2025/0161660 | A1 | 5/2025 | Baumbach et al. |
| 2025/0170388 | A1 | 5/2025 | Kerkhoffs et al. |
| 2025/0339669 | A1 | 11/2025 | Stotz et al. |

FOREIGN PATENT DOCUMENTS

| | | | |
|---|---|---|---|
| AU | 2012261669 | | 1/2013 |
| AU | 2013203301 | | 5/2013 |
| AU | 2013273663 | | 1/2014 |
| BR | PI0904483-3 | | 7/2011 |
| CA | 2 026 692 | | 4/1992 |
| CA | 2 026 693 | | 4/1992 |
| CA | 2 292 432 | | 5/1998 |
| CA | 2 664 835 | | 2/2008 |
| CA | 2 796 357 | | 10/2011 |
| CA | 2 947 984 | | 11/2022 |
| CN | 1222862 | A | 7/1999 |
| CN | 1254598 | A | 5/2000 |
| CN | 1376523 | A | 10/2002 |
| CN | 2535055 | | 2/2003 |
| CN | 1118304 | C | 8/2003 |
| CN | 2616217 | | 5/2004 |
| CN | 1202871 | C | 5/2005 |
| CN | 1833736 | A | 9/2006 |
| CN | 200977306 | | 11/2007 |
| CN | 101112628 | | 1/2008 |
| CN | 101128168 | | 2/2008 |
| CN | 201150675 | | 11/2008 |
| CN | 101677812 | | 3/2010 |
| CN | 201437016 | | 4/2010 |
| CN | 201618200 | | 11/2010 |
| CN | 201658687 | | 12/2010 |
| CN | 201710717 | | 1/2011 |
| CN | 201894758 | | 7/2011 |
| CN | 102475923 | | 5/2012 |
| CN | 102545538 | | 7/2012 |
| CN | 202314596 | | 7/2012 |
| CN | 102743801 | | 10/2012 |
| CN | 103143072 | | 6/2013 |
| CN | 103845766 | | 6/2014 |
| CN | 103861162 | | 6/2014 |
| CN | 103915980 | | 7/2014 |
| CN | 203809157 | | 9/2014 |
| CN | 203842087 | | 9/2014 |
| CN | 104208763 | | 12/2014 |
| CN | 104208764 | | 12/2014 |
| CN | 203971004 | | 12/2014 |
| CN | 104274873 | | 1/2015 |
| CN | 204106671 | | 1/2015 |
| CN | 204219479 | | 3/2015 |
| CN | 103877630 | | 2/2016 |
| CN | 205215814 | | 5/2016 |
| CN | 103977464 | | 8/2016 |
| CN | 104162192 | | 9/2016 |
| CN | 104888293 | | 3/2017 |
| CN | 106512117 | | 3/2017 |
| CN | 104225696 | | 6/2017 |
| CN | 107019824 | | 8/2017 |
| CN | 206443963 | | 8/2017 |
| CN | 107281567 | | 10/2017 |
| CN | 104707194 | | 11/2017 |
| CN | 107921187 | | 4/2018 |
| CN | 105498002 | | 6/2018 |
| CN | 106310410 | | 7/2018 |
| CN | 106902404 | | 8/2019 |
| CN | 209790495 | | 12/2019 |
| CN | 110665079 | | 1/2020 |
| CN | 210020563 | | 2/2020 |
| CN | 111166948 | | 5/2020 |
| CN | 111166949 | | 5/2020 |
| CN | 215841206 | | 2/2022 |
| CN | 217828630 | | 11/2022 |
| CN | 218922664 | | 4/2023 |
| CN | 116077106 | | 5/2023 |
| CN | 116365757 | | 6/2023 |
| CN | 219250364 | | 6/2023 |
| CN | 116785582 | | 9/2023 |
| CN | 116531654 | | 11/2023 |
| CN | 116440404 | | 3/2024 |
| CN | 117018427 | | 3/2024 |
| CN | 117482377 | | 4/2024 |
| CN | 118320293 | | 7/2024 |
| CN | 118320294 | | 7/2024 |
| CN | 113769260 | | 9/2024 |
| CN | 118142074 | | 9/2024 |
| CN | 118681125 | | 9/2024 |
| CN | 118899971 | | 11/2024 |
| DE | 1 001 642 | | 1/1957 |
| DE | 1 165 144 | | 3/1964 |
| DE | 27 07 951 | | 9/1977 |
| DE | 26 24 058 | | 12/1977 |
| DE | 3 545 214 | | 7/1986 |
| DE | 41 05 278 | | 8/1992 |
| DE | 195 46 336 | | 5/1997 |

(56) References Cited

FOREIGN PATENT DOCUMENTS

| | | |
|---|---|---|
| DE | 695 01 834 | 10/1998 |
| DE | 198 54 724 | 5/1999 |
| DE | 198 21 307 | 10/1999 |
| DE | 199 10 872 | 10/1999 |
| DE | 199 56 380 | 11/1999 |
| DE | 100 59 714 | 5/2002 |
| DE | 103 45 694 | 4/2005 |
| DE | 697 31 709 | 4/2005 |
| DE | 101 55 011 | 11/2005 |
| DE | 601 19 592 | 9/2006 |
| DE | 11 2004 001 809 | 11/2006 |
| DE | 20 2005 020 288 | 6/2007 |
| DE | 10 2006 019 206 | 10/2007 |
| DE | 10 2006 036 948 | 2/2008 |
| DE | 10 2008 060 357 | 6/2010 |
| DE | 10 2009 039 658 | 3/2011 |
| DE | 20 2009 018 416 | 8/2011 |
| DE | 10 2010 041 995 | 4/2012 |
| DE | 10 2012 022 456 | 5/2014 |
| DE | 10 2013 007 562 | 11/2014 |
| DE | 10 2014 210 299 | 12/2015 |
| DE | 10 2014 212 323 | 12/2015 |
| DE | 11 2014 001 418 | 12/2015 |
| DE | 10 2014 224 151 | 6/2016 |
| DE | 10 2015 216 050 | 2/2017 |
| DE | 10 2015 219 263 | 4/2017 |
| DE | 10 2015 222 199 | 5/2017 |
| DE | 20 2015 009 422 | 7/2017 |
| DE | 10 2012 207 042 | 9/2017 |
| DE | 10 2016 013 334 | 4/2018 |
| DE | 10 2017 209 917 | 12/2018 |
| DE | 10 2017 212 193 | 1/2019 |
| DE | 10 2018 207 564 | 11/2019 |
| DE | 10 2018 207 578 | 11/2019 |
| DE | 10 2018 207 585 | 11/2019 |
| DE | 10 2018 207 591 | 11/2019 |
| DE | 10 2018 207 594 | 11/2019 |
| DE | 10 2018 207 611 | 11/2019 |
| DE | 10 2018 207 622 | 11/2019 |
| DE | 10 2018 208 536 | 12/2019 |
| DE | 10 2018 208 540 | 12/2019 |
| DE | 10 2018 208 541 | 12/2019 |
| DE | 10 2018 208 550 | 12/2019 |
| DE | 10 2018 208 945 | 12/2019 |
| DE | 10 2018 210 076 | 12/2019 |
| DE | 10 2018 207 624 | 1/2020 |
| DE | 10 2018 211 327 | 1/2020 |
| DE | 10 2018 211 328 | 1/2020 |
| DE | 10 2018 212 153 | 1/2020 |
| DE | 10 2018 213 350 | 2/2020 |
| DE | 10 2018 220 658 | 6/2020 |
| DE | 10 2020 102 473 | 8/2021 |
| DE | 11 2020 003 063 | 3/2022 |
| DE | 11 2020 004 148 | 6/2022 |
| EP | 0 050 814 | 5/1982 |
| EP | 0 629 412 | 12/1994 |
| EP | 0 764 448 | 3/1997 |
| EP | 0 855 515 | 7/1998 |
| EP | 0 890 179 | 1/1999 |
| EP | 0 904 630 | 3/1999 |
| EP | 0 916 359 | 5/1999 |
| EP | 1 013 294 | 6/2000 |
| EP | 1 186 873 | 3/2002 |
| EP | 1 475 880 | 11/2004 |
| EP | 1 169 072 | 5/2005 |
| EP | 1 176 999 | 7/2005 |
| EP | 1 801 420 | 6/2007 |
| EP | 2 009 233 | 12/2008 |
| EP | 2 098 746 | 9/2009 |
| EP | 2 047 872 | 9/2010 |
| EP | 2 403 109 | 1/2012 |
| EP | 2 187 807 | 6/2012 |
| EP | 2 330 724 | 8/2012 |
| EP | 3 326 567 | 10/2014 |
| EP | 1 898 971 | 3/2015 |
| EP | 2 519 273 | 8/2015 |
| EP | 2 217 302 | 9/2015 |
| EP | 2 438 936 | 10/2015 |
| EP | 2 438 937 | 10/2015 |
| EP | 2 960 515 | 12/2015 |
| EP | 2 968 718 | 1/2016 |
| EP | 1 996 252 | 5/2016 |
| EP | 2 475 415 | 6/2016 |
| EP | 2 906 265 | 7/2016 |
| EP | 3 069 739 | 9/2016 |
| EP | 1 931 403 | 1/2017 |
| EP | 3 127 562 | 2/2017 |
| EP | 2 585 129 | 3/2017 |
| EP | 2 646 068 | 3/2017 |
| EP | 3 187 210 | 7/2017 |
| EP | 3 222 301 | 9/2017 |
| EP | 3 222 302 | 9/2017 |
| EP | 3 020 426 | 12/2017 |
| EP | 3 038 669 | 1/2018 |
| EP | 3 062 730 | 1/2018 |
| EP | 3 180 050 | 2/2018 |
| EP | 3 287 154 | 2/2018 |
| EP | 1 789 129 | 6/2018 |
| EP | 2 366 412 | 8/2018 |
| EP | 3 205 359 | 8/2018 |
| EP | 3 205 360 | 8/2018 |
| EP | 3 131 599 | 2/2019 |
| EP | 3 456 367 | 3/2019 |
| EP | 3 119 451 | 6/2019 |
| EP | 3 528 865 | 8/2019 |
| EP | 3 536 360 | 9/2019 |
| EP | 3 542 835 | 9/2019 |
| EP | 3 542 836 | 9/2019 |
| EP | 3 062 877 | 12/2019 |
| EP | 3 189 862 | 2/2020 |
| EP | 3 668 560 | 6/2020 |
| EP | 3 687 625 | 8/2020 |
| EP | 3 711 785 | 9/2020 |
| EP | 3 711 786 | 9/2020 |
| EP | 3 711 787 | 9/2020 |
| EP | 3 720 520 | 10/2020 |
| EP | 3 069 738 | 12/2020 |
| EP | 3 069 740 | 12/2020 |
| EP | 3 131 597 | 12/2020 |
| EP | 3 142 722 | 12/2020 |
| EP | 3 579 894 | 12/2020 |
| EP | 3 188 769 | 1/2021 |
| EP | 3 490 122 | 1/2021 |
| EP | 2 869 866 | 2/2021 |
| EP | 3 398 626 | 2/2021 |
| EP | 3 487 549 | 2/2021 |
| EP | 3 113 806 | 3/2021 |
| EP | 3 615 103 | 3/2021 |
| EP | 4 271 461 | 3/2021 |
| EP | 2 344 218 | 4/2021 |
| EP | 3 436 104 | 4/2021 |
| EP | 3 749 383 | 4/2021 |
| EP | 3 808 404 | 4/2021 |
| EP | 3 821 938 | 5/2021 |
| EP | 3 131 615 | 6/2021 |
| EP | 3 338 825 | 6/2021 |
| EP | 3 432 944 | 6/2021 |
| EP | 3 684 439 | 7/2021 |
| EP | 2 582 414 | 8/2021 |
| EP | 3 407 930 | 8/2021 |
| EP | 3 782 665 | 8/2021 |
| EP | 3 782 666 | 8/2021 |
| EP | 3 782 668 | 8/2021 |
| EP | 3 858 397 | 8/2021 |
| EP | 3 216 467 | 9/2021 |
| EP | 3 463 505 | 9/2021 |
| EP | 3 884 968 | 9/2021 |
| EP | 3 884 969 | 9/2021 |
| EP | 3 027 241 | 10/2021 |
| EP | 3 579 904 | 11/2021 |
| EP | 2 628 493 | 12/2021 |
| EP | 3 914 330 | 12/2021 |
| EP | 3 928 825 | 12/2021 |
| EP | 3 556 409 | 1/2022 |

(56) References Cited

FOREIGN PATENT DOCUMENTS

| | | |
|---|---|---|
| EP | 3 624 868 | 1/2022 |
| EP | 3 930 785 | 1/2022 |
| EP | 3 955 985 | 2/2022 |
| EP | 3 624 867 | 3/2022 |
| EP | 3 689 389 | 3/2022 |
| EP | 3 697 464 | 3/2022 |
| EP | 3 737 436 | 3/2022 |
| EP | 3 972 661 | 3/2022 |
| EP | 2 967 630 | 4/2022 |
| EP | 3 142 721 | 4/2022 |
| EP | 3 520 834 | 4/2022 |
| EP | 3 586 887 | 4/2022 |
| EP | 3 638 336 | 4/2022 |
| EP | 3 689 388 | 4/2022 |
| EP | 3 765 110 | 4/2022 |
| EP | 3 782 667 | 4/2022 |
| EP | 3 829 673 | 4/2022 |
| EP | 3 976 129 | 4/2022 |
| EP | 3 984 589 | 4/2022 |
| EP | 3 986 528 | 4/2022 |
| EP | 3 649 926 | 5/2022 |
| EP | 3 653 113 | 5/2022 |
| EP | 3 654 006 | 5/2022 |
| EP | 3 735 280 | 5/2022 |
| EP | 3 897 814 | 5/2022 |
| EP | 3 219 339 | 6/2022 |
| EP | 3 737 310 | 7/2022 |
| EP | 3 899 994 | 8/2022 |
| EP | 4 039 320 | 8/2022 |
| EP | 3 487 550 | 9/2022 |
| EP | 3 606 575 | 9/2022 |
| EP | 3 834 876 | 9/2022 |
| EP | 3 000 492 | 10/2022 |
| EP | 3 600 477 | 10/2022 |
| EP | 3 897 768 | 10/2022 |
| EP | 3 914 310 | 10/2022 |
| EP | 3 914 311 | 10/2022 |
| EP | 3 000 493 | 11/2022 |
| EP | 3 858 422 | 11/2022 |
| EP | 3 866 876 | 11/2022 |
| EP | 3 941 546 | 11/2022 |
| EP | 2 892 583 | 1/2023 |
| EP | 3 393 542 | 1/2023 |
| EP | 3 597 231 | 1/2023 |
| EP | 3 656 292 | 1/2023 |
| EP | 3 768 345 | 1/2023 |
| EP | 2 868 332 | 2/2023 |
| EP | 3 003 420 | 2/2023 |
| EP | 3 539 585 | 2/2023 |
| EP | 3 956 010 | 2/2023 |
| EP | 4 137 193 | 2/2023 |
| EP | 3 046 594 | 3/2023 |
| EP | 3 127 563 | 3/2023 |
| EP | 3 256 186 | 3/2023 |
| EP | 3 288 609 | 3/2023 |
| EP | 3 538 173 | 3/2023 |
| EP | 3 606 576 | 3/2023 |
| EP | 3 927 390 | 3/2023 |
| EP | 3 384 940 | 4/2023 |
| EP | 3 441 616 | 4/2023 |
| EP | 3 938 005 | 4/2023 |
| EP | 3 946 511 | 4/2023 |
| EP | 3 544 649 | 6/2023 |
| EP | 3 634 528 | 6/2023 |
| EP | 3 809 959 | 7/2023 |
| EP | 3 912 673 | 7/2023 |
| EP | 4 218 897 | 8/2023 |
| EP | 4 218 898 | 8/2023 |
| EP | 4 218 899 | 8/2023 |
| EP | 2 961 984 | 9/2023 |
| EP | 3 352 808 | 9/2023 |
| EP | 3 554 576 | 10/2023 |
| EP | 3 615 102 | 10/2023 |
| EP | 3 737 435 | 10/2023 |
| EP | 3 795 208 | 10/2023 |
| EP | 4 052 754 | 10/2023 |
| EP | 4 149 606 | 10/2023 |
| EP | 3 157 596 | 11/2023 |
| EP | 3 515 525 | 11/2023 |
| EP | 3 621 669 | 11/2023 |
| EP | 3 744 362 | 11/2023 |
| EP | 3 766 428 | 11/2023 |
| EP | 3 808 390 | 11/2023 |
| EP | 4 061 470 | 11/2023 |
| EP | 3 449 958 | 12/2023 |
| EP | 3 687 596 | 12/2023 |
| EP | 3 710 076 | 12/2023 |
| EP | 3 768 340 | 12/2023 |
| EP | 3 787 707 | 12/2023 |
| EP | 3 926 194 | 12/2023 |
| EP | 3 784 305 | 1/2024 |
| EP | 3 801 675 | 1/2024 |
| EP | 3 925 659 | 1/2024 |
| EP | 4 115 919 | 1/2024 |
| EP | 3 634 526 | 2/2024 |
| EP | 3 768 342 | 2/2024 |
| EP | 3 768 347 | 2/2024 |
| EP | 3 769 799 | 2/2024 |
| EP | 3 790 606 | 2/2024 |
| EP | 3 930 780 | 2/2024 |
| EP | 3 782 695 | 3/2024 |
| EP | 3 854 448 | 3/2024 |
| EP | 4 140 532 | 5/2024 |
| EP | 3 693 038 | 6/2024 |
| EP | 3 768 344 | 7/2024 |
| EP | 3 970 765 | 7/2024 |
| EP | 4 419 042 | 8/2024 |
| EP | 3 854 444 | 9/2024 |
| EP | 4 384 259 | 9/2024 |
| EP | 4 429 750 | 9/2024 |
| EP | 3 534 985 | 10/2024 |
| EP | 3 793 674 | 10/2024 |
| EP | 3 893 957 | 10/2024 |
| EP | 3 914 334 | 10/2024 |
| EP | 3 618 885 | 11/2024 |
| EP | 4 034 221 | 11/2024 |
| EP | 4 087 641 | 11/2024 |
| EP | 4 039 289 | 12/2024 |
| EP | 4 084 856 | 1/2025 |
| EP | 3 522 947 | 2/2025 |
| EP | 4 429 754 | 2/2025 |
| EP | 3 998 102 | 3/2025 |
| EP | 4 429 751 | 3/2025 |
| EP | 4 429 752 | 3/2025 |
| EP | 4 429 753 | 3/2025 |
| EP | 4 023 282 | 4/2025 |
| EP | 3 950 043 | 5/2025 |
| EP | 3 955 986 | 5/2025 |
| EP | 3 958 921 | 5/2025 |
| EP | 3 990 047 | 5/2025 |
| EP | 4 218 900 | 5/2025 |
| EP | 4 429 755 | 5/2025 |
| EP | 2 830 675 | 6/2025 |
| EP | 3 965 845 | 6/2025 |
| EP | 4 039 319 | 6/2025 |
| EP | 3 668 558 | 7/2025 |
| EP | 3 780 041 | 7/2025 |
| EP | 4 095 872 | 7/2025 |
| EP | 3 668 559 | 8/2025 |
| EP | 3 746 149 | 8/2025 |
| EP | 3 823 687 | 8/2025 |
| EP | 3 848 088 | 8/2025 |
| EP | 4 119 184 | 9/2025 |
| EP | 4 218 556 | 9/2025 |
| EP | 4 046 678 | 10/2025 |
| EP | 4 034 192 | 12/2025 |
| EP | 4 100 106 | 12/2025 |
| EP | 4 134 123 | 1/2026 |
| EP | 4 201 467 | 1/2026 |
| EP | 4 233 989 | 1/2026 |
| FR | 1458525 | 3/1966 |
| FR | 2 768 056 | 3/1999 |
| GB | 0 648 739 | 1/1951 |
| GB | 2 213 541 | 8/1989 |

(56) References Cited

FOREIGN PATENT DOCUMENTS

| | | | |
|---|---|---|---|
| GB | 2 345 387 | | 7/2000 |
| GB | 2 451 161 | | 12/2011 |
| GB | 2 504 177 | | 1/2014 |
| GB | 2 545 062 | | 6/2017 |
| GB | 2 545 750 | | 6/2017 |
| JP | 59-119788 | | 8/1984 |
| JP | S61-500059 | | 1/1986 |
| JP | S62-113555 | | 7/1987 |
| JP | S64-68236 | | 3/1989 |
| JP | H02-055886 | | 2/1990 |
| JP | 2-79738 | | 3/1990 |
| JP | H04-176471 | | 6/1992 |
| JP | H04-108384 | | 9/1992 |
| JP | H08-057042 | | 3/1996 |
| JP | H08-504621 | | 5/1996 |
| JP | H10-052489 | | 2/1998 |
| JP | 2888609 | | 5/1999 |
| JP | 2889384 | | 5/1999 |
| JP | H11-239617 | | 9/1999 |
| JP | 2001-037728 | | 2/2001 |
| JP | 2001-515374 | | 9/2001 |
| JP | 2001-515375 | | 9/2001 |
| JP | 2003-019197 | | 1/2003 |
| JP | 2003-525438 | | 8/2003 |
| JP | 2003-528697 | | 9/2003 |
| JP | 2004-019468 | | 1/2004 |
| JP | 2004-515278 | | 5/2004 |
| JP | 2004-278375 | | 10/2004 |
| JP | 2005-028137 | | 2/2005 |
| JP | 2005-507039 | | 3/2005 |
| JP | 2007-222644 | | 9/2007 |
| JP | 2008-511414 | | 4/2008 |
| JP | 2008-516654 | | 5/2008 |
| JP | 2010-503495 | | 2/2010 |
| JP | 2010-518907 | | 6/2010 |
| JP | 2010-258181 | | 11/2010 |
| JP | 2010-534080 | | 11/2010 |
| JP | 2013-013216 | | 1/2013 |
| JP | 2013-519497 | | 5/2013 |
| JP | 2014-004303 | | 1/2014 |
| JP | 2014-524274 | | 9/2014 |
| JP | 2015-514529 | | 5/2015 |
| JP | 2015-514531 | | 5/2015 |
| JP | 2015-122448 | | 7/2015 |
| JP | 2016-002466 | | 1/2016 |
| JP | 2016-532500 | | 10/2016 |
| JP | 6063151 | | 1/2017 |
| JP | 6267625 | | 1/2018 |
| JP | 2018-057878 | | 4/2018 |
| JP | 2019-508128 | | 3/2019 |
| JP | 2019-516458 | | 6/2019 |
| JP | 6572056 | | 9/2019 |
| JP | 2020-072985 | | 5/2020 |
| JP | 2020-523090 | | 8/2020 |
| JP | 2018-510708 | | 3/2021 |
| JP | 2019-509141 | | 2/2022 |
| KR | 10-2011-0098192 | | 9/2011 |
| RO | 131676 | | 2/2017 |
| RU | 2 051 695 | | 1/1996 |
| TW | 374317 | | 11/1999 |
| UA | 97202 | C2 | 1/2012 |
| WO | WO 94/009835 | | 5/1994 |
| WO | WO 97/037696 | | 10/1997 |
| WO | WO 97/039785 | | 10/1997 |
| WO | WO 99/049912 | | 10/1999 |
| WO | WO 00/033446 | | 6/2000 |
| WO | WO 02/022200 | | 3/2002 |
| WO | WO 02/041935 | | 5/2002 |
| WO | WO 02/070039 | | 9/2002 |
| WO | WO 03/075981 | | 9/2003 |
| WO | WO 03/103745 | | 12/2003 |
| WO | WO 2005/020848 | | 3/2005 |
| WO | WO 2005/028014 | | 3/2005 |
| WO | WO 2005/037345 | | 4/2005 |
| WO | WO 2007/033933 | | 3/2007 |
| WO | WO 2007/105842 | | 9/2007 |
| WO | WO 2008/017289 | | 2/2008 |
| WO | WO 2008/081783 | | 7/2008 |
| WO | WO 2009/010888 | | 1/2009 |
| WO | WO 2009/046789 | | 4/2009 |
| WO | WO 2009/046790 | | 4/2009 |
| WO | WO 2009/073037 | | 6/2009 |
| WO | WO 2010/119267 | | 10/2010 |
| WO | WO 2011/003043 | | 1/2011 |
| WO | WO 2011/081626 | | 7/2011 |
| WO | WO 2011/160858 | | 12/2011 |
| WO | WO 2012/018917 | | 2/2012 |
| WO | WO 2012/047540 | | 4/2012 |
| WO | WO 2012/112129 | | 8/2012 |
| WO | WO 2013/037380 | | 3/2013 |
| WO | WO 2013/120957 | | 8/2013 |
| WO | WO 2013/167432 | | 11/2013 |
| WO | WO 2013/173239 | | 11/2013 |
| WO | WO 2014/042925 | | 3/2014 |
| WO | WO 2015/039605 | | 3/2015 |
| WO | WO 2015/063281 | | 5/2015 |
| WO | WO 2015/085076 | | 6/2015 |
| WO | WO 2015/109028 | | 7/2015 |
| WO | WO 2015/172173 | | 11/2015 |
| WO | WO 2015/175718 | | 11/2015 |
| WO | WO 2016/028644 | | 2/2016 |
| WO | WO 2016/137743 | | 9/2016 |
| WO | WO 2016/146661 | | 9/2016 |
| WO | WO 2016/146663 | | 9/2016 |
| WO | WO 2017/004175 | | 1/2017 |
| WO | WO 2017/015764 | | 2/2017 |
| WO | WO 2017/021465 | | 2/2017 |
| WO | WO 2017/053988 | | 3/2017 |
| WO | WO 2017/060257 | | 4/2017 |
| WO | WO 2017/112695 | | 6/2017 |
| WO | WO 2017/112698 | | 6/2017 |
| WO | WO 2017/147291 | | 8/2017 |
| WO | WO 2017/159849 | | 9/2017 |
| WO | WO 2017/162619 | | 9/2017 |
| WO | WO 2017/205909 | | 12/2017 |
| WO | WO 2018/007120 | | 1/2018 |
| WO | WO 2018/036927 | | 3/2018 |
| WO | WO 2018/039479 | | 3/2018 |
| WO | WO 2018/088939 | | 3/2018 |
| WO | WO 2018/081040 | | 5/2018 |
| WO | WO 2018/089970 | | 5/2018 |
| WO | WO 2018/109038 | | 6/2018 |
| WO | WO 2018/139508 | | 8/2018 |
| WO | WO 2018/197306 | | 11/2018 |
| WO | WO 2019/034670 | | 2/2019 |
| WO | WO 2019/035804 | | 2/2019 |
| WO | WO 2019/038343 | | 2/2019 |
| WO | WO 2019/057636 | | 3/2019 |
| WO | WO 2019/067233 | | 4/2019 |
| WO | WO 2019/078723 | | 4/2019 |
| WO | WO 2019/135767 | | 7/2019 |
| WO | WO 2019/137911 | | 7/2019 |
| WO | WO 2019/138350 | | 7/2019 |
| WO | WO 2019/145253 | | 8/2019 |
| WO | WO 2019/158996 | | 8/2019 |
| WO | WO 2019/161245 | | 8/2019 |
| WO | WO 2019/180104 | | 9/2019 |
| WO | WO 2019/180179 | | 9/2019 |
| WO | WO 2019/180181 | | 9/2019 |
| WO | WO 2019/191245 | | 10/2019 |
| WO | WO 2018/135477 | | 11/2019 |
| WO | WO 2018/135478 | | 11/2019 |
| WO | WO 2019/211410 | | 11/2019 |
| WO | WO 2019/219868 | | 11/2019 |
| WO | WO 2019/219871 | | 11/2019 |
| WO | WO 2019/219872 | | 11/2019 |
| WO | WO 2019/219874 | | 11/2019 |
| WO | WO 2019/219876 | | 11/2019 |
| WO | WO 2019/219881 | | 11/2019 |
| WO | WO 2019/219882 | | 11/2019 |
| WO | WO 2019/219883 | | 11/2019 |
| WO | WO 2019/219884 | | 11/2019 |
| WO | WO 2019/219885 | | 11/2019 |
| WO | WO 2019/229210 | | 12/2019 |

(56) References Cited

FOREIGN PATENT DOCUMENTS

| | | |
|---|---|---|
| WO | WO 2019/229211 | 12/2019 |
| WO | WO 2019/229214 | 12/2019 |
| WO | WO 2019/229220 | 12/2019 |
| WO | WO 2019/229221 | 12/2019 |
| WO | WO 2019/229222 | 12/2019 |
| WO | WO 2019/229223 | 12/2019 |
| WO | WO 2019/229224 | 12/2019 |
| WO | WO 2019/234146 | 12/2019 |
| WO | WO 2019/239259 | 12/2019 |
| WO | WO 2019/241556 | 12/2019 |
| WO | WO 2019/243582 | 12/2019 |
| WO | WO 2019/243588 | 12/2019 |
| WO | WO 2020/003110 | 1/2020 |
| WO | WO 2020/011760 | 1/2020 |
| WO | WO 2020/011795 | 1/2020 |
| WO | WO 2020/011797 | 1/2020 |
| WO | WO 2020/016438 | 1/2020 |
| WO | WO 2020/028312 | 2/2020 |
| WO | WO 2020/028537 | 2/2020 |
| WO | WO 2020/030700 | 2/2020 |
| WO | WO 2020/064911 | 4/2020 |
| WO | WO 2020/073047 | 4/2020 |
| WO | WO 2020/132211 | 6/2020 |
| WO | WO 2020/176236 | 9/2020 |
| WO | WO 2020/187797 | 9/2020 |
| WO | WO 2020/219430 | 10/2020 |
| WO | WO 2020/234785 | 11/2020 |
| WO | WO 2020/242881 | 12/2020 |
| WO | WO 2020/264174 | 12/2020 |
| WO | WO 2021/046275 | 3/2021 |
| WO | WO 2021/062265 | 4/2021 |
| WO | WO 2021/067691 | 4/2021 |
| WO | WO 2021/119478 | 6/2021 |
| WO | WO 2021/150777 | 7/2021 |
| WO | WO 2021/152013 | 8/2021 |
| WO | WO 2021/191106 | 9/2021 |
| WO | WO 2023/040546 | 12/2021 |
| WO | WO 2022/056542 | 3/2022 |
| WO | WO 2022/063650 | 3/2022 |
| WO | WO 2022/072944 | 4/2022 |
| WO | WO 2022/076862 | 4/2022 |
| WO | WO 2022/076948 | 4/2022 |
| WO | WO 2022/109589 | 5/2022 |
| WO | WO 2022/109590 | 5/2022 |
| WO | WO 2022/109591 | 5/2022 |
| WO | WO 2022/173970 | 8/2022 |
| WO | WO 2022/173977 | 8/2022 |
| WO | WO 2022/174249 | 8/2022 |
| WO | WO 2023/226779 | 9/2022 |
| WO | WO 2023/278599 | 1/2023 |
| WO | WO 2023/014742 | 2/2023 |
| WO | WO 2023/037162 | 3/2023 |
| WO | WO 2023/049813 | 3/2023 |
| WO | WO 2024/160098 | 4/2023 |
| WO | WO 2023/076461 | 5/2023 |
| WO | WO 2023/076869 | 5/2023 |
| WO | WO 2023/230157 | 11/2023 |
| WO | WO 2024/104184 | 5/2024 |
| WO | WO 2024/243154 | 11/2024 |
| WO | WO 2025/226734 | 10/2025 |

OTHER PUBLICATIONS

T. Hinkel and M. Giffrow; "Pump Reliability and Efficiency Increase Maintenance Program—Utilizing High Performance Thermoplastics;" Proceedings of the 16th International Pump Users Symposium, Texas A&M University. Turbomachinery Laboratories, p. 115-120; 1999. (Year: 1999).*

A. Escudeiro, M.A. Wimmer, T. Polcar, A. Cavaleiro; "Tribological behavior of uncoated and DLC-coated CoCr and Ti-alloys in contact with UHMWPE and PEEK counterbodies;" Tribology International, vol. 89, 2015, pp. 97-104. (Year: 2015).*

Anita Sak et al.; "Influence of polyetheretherketone coatings on the Ti—13Nb—13Zr titanium alloy's bio-tribological properties and corrosion resistance;" Materials Science and Engineering: C, vol. 63, 2016, pp. 52-61 (Year: 2016).*

McMaster-Carr Online Catalog, "Slide Bearings search results;" https://www.mcmaster.com/products/slide-bearings/; accessed Oct. 24, 2024. (Year: 2024).*

GGB by Timken Bearings FAQ; "What is a Slide Bearing ?;" https://www.ggbearings.com/en/why-choose-ggb/faq/bearings-faq/what-slide-bearing; accessed Oct. 18, 2024. (Year: 2024).*

RBCBearings.com, "RBC Bearings Incorporated—Products;" https://www.rbcbearings.com/Products; accessed Oct. 18, 2024. (Year: 2024).*

McMaster-Carr Online Catalog, "Bearings search results;" https://www.mcmaster.com/products/bearings/; accessed Oct. 18, 2024 (Year: 2024).*

SKF.com; "Products: Bearings;" https://www.skf.com/us/products/bearings; accessed Oct. 18, 2024. (Year: 2024).*

Ai, X. (2013). Radial Bearings. In: Wang, Q.J., Chung, YW. (eds) Encyclopedia of Tribology. Springer, Boston, MA. https://doi.org/10.1007/978-0-387-92897-5_334, accessed Oct. 18, 2024 (Year: 2024).*

Wikipedia, "Plain Bearing," https://en.wikipedia.org/wiki/Plain_bearing; accessed Oct. 18, 2024. (Year: 2024).*

Google.com, "Spider Bearing—Search Results;" https://www.google.com/search?q=spider+bearing&rlz=1C1GCEA_enUS1059US1059&oq=spider+beari&gs_lcrp=EgZjaHJvbWUqCQgAEEUYOxiABDIJCAAQRRg7GIAEMgYIARBFGDkyBwgCEAAYgAQyBwgDEAAYgAQyBwgEEAAYgAQyBwgFEAAYgAQyBwgGEAAYgAQyBggHEEUYPKgCALACAA&sourceid=chrome&ie=UTF-8 (Year: 2024).*

New Hampshire Ball Bearings, Inc., "Self-Lubricating Liner Systems," https://www.nhbb.com/index.php/knowledge-center/engineering-reference/rod-end-spherical-bearings/self-lubricating-liner-systems, accessed Nov. 7, 2025 (Year: 2024).*

International Search Report and Written Opinion received in PCT Application No. PCT/EP2019/076002, dated Dec. 20, 2019 in 11 pages.

International Preliminary Report on Patentability and Written Opinion received in PCT Application No. PCT/EP2019/076002, dated Apr. 8, 2021 in 7 pages.

"ABMD—Taking a Closer Look at Impella ECP as the Pivotal Trial Gets Underway", Guggenheim, Press Release, Mar. 29, 2022, pp. 4.

"Edwards SAPIEN 3 Kit—Transapical and Transaortic", Edwards Lifesciences, Released Nov. 8, 2016, pp. 11. chrome-extension://efaidnbmnnnibpcajpcglclefindmkaj/https://edwardsprod.blob.core.windows.net/media/De/sapien3/doc-0045537b%20-%20certitude.pdf.

Park et al., "A Novel Electrical Potential Sensing Method for in Vitro Stent Fracture Monitoring and Detection", Jan. 1, 2011, vol. 21, No. 4, pp. 213-222.

Vollkron et al., "Advanced Suction Detection for an Axial Flow Pump", Artificial Organs, 2006, vol. 30, No. 9, pp. 665-670.

Vollkron et al., "Development of a Suction Detection System for Axial Blood Pumps", Artificial Organs, 2004, vol. 28, No. 8, pp. 709-716.

Gopinath, Divya, "A System for Impedance Characterization of Coronary Stents", University of Strathclyde Engineering, Thesis, Aug. 2015, pp. 77.

Delgado et al., "Interventional Treatment of Advanced Ischemic Heart Disease", Percutaneous Mechanical Assist Devices, Ch. 6, Springer, 2009, pp. 85-91.

Delgado et al., "Interventional Treatment of Advanced Ischemic Heart Disease", The Future of Treatment of Advanced Ischemic Heart Disease, Ch. 8, Springer, 2009, pp. 129-142.

Eeckhout, MD, PhD, et al., "Handbook of Complications During Percutaneous Cardiovascular Interventions", 2007 Informa UK Ltd., Ch. 12, pp. 167-177.

"FDA Approves Abiomed's Heart Pump Impella, Shares Rise", Reuters 2008 press release, Jun. 2, 2008, https://jp.reuters.com/article/us-abiomed/fda-approves-abiomeds-heart-pump-impella-shares-rise-idUSBNG131420080602/, 1 page.

(56) References Cited

OTHER PUBLICATIONS

Lake et al., "Pediatric Cardiac Anesthesia", 4th Edition, 2005, Ch. 15, pp. 291-303.
Machiraju, Venkat R., "Redo Cardiac Surgery in Adults", Practical Approaches to the Current "On-Pump" Redo Coronary Artery Bypass Surgery, Ch. 2, Springer, 2012, pp. 7-19.
Machiraju, Venkat R., "Redo Cardiac Surgery in Adults", Options for Advanced Mechanical Support for Cardiogenic Shock Complicating Cardiac Reoperations, Ch. 9, Springer, 2012, pp. 67-80.
Machiraju, Venkat R., "Redo Cardiac Surgery in Adults", Percutaneous Approaches to Valvular Heart Disease After Previous Cardiac Surgery, Ch. 21, Springer, 2012, pp. 195-200.
Parrillo et al., "Critical Care Medicine", Principles of Diagnosis and Management in the Adult, Elsevier, 4th Edition, 2014, Chapters 4 & 29, pp. 47-58.e1 and 442-469.e4.
Vincent, MD, Phd, et al., "Textbook of Critical Care", Acute Coronary Syndromes: Therapy, Elsevier, 7th Edition, Ch. 78, 2017, pp. 520-531.e3.
Vincent, MD, PhD, et al., "Textbook of Critical Care", Mechanical Support in Cardiogenic Shock, Elsevier, 7th Edition, Ch. 91, 2017, pp. 637-648.e3.
Schmitz-Rode, T, Graf, J, Pfeffer, J. et al. "An Expandable Percutaneous Catheter Pump for Left Ventricular Support: Proof of Concept", JACC. Jun. 2005, 45 (11) 1856-1861.

* cited by examiner 10
11
14
13
14
22
19
20
$F_{mag}$
12
$F_{hyd}$
21
15
17
18
190
16

SEALED MICROPUMP

BACKGROUND

Field

The present invention relates to a sealed micropump comprising an integrated motor and at least one impeller for producing a fluid flow inside a housing of the micropump.

Description of the Related Art

To provide cardiovascular support for patients having heart failure, systems are used that take over part of the pumping function or even all of the pumping function of the heart. In addition to systems that are seated on the outside of the heart, which are implanted invasively, systems are also known that are inserted minimally invasively as mechanical pumps, in particular into the left ventricle of the heart and the adjoining aorta. Continuous pumping pumps blood from the left ventricle into the aorta, so that enough oxygen-rich blood can circulate in the body of a heart failure patient. The US patent application US 2013/0303833 A1, for example, describes an implantable blood pump, in which a blood flow is produced within the housing by a rotor disposed inside.

Because they are minimally invasively implanted, these systems have to be very small, in particular in terms of their radial circumference, for example having an outer diameter of no more 10 mm. These requirements for miniaturization of the components present a major challenge.

SUMMARY

The underlying object of the invention is to further improve the micropumps and systems known in the state of the art and achieve the highest possible efficiencies for delivering fluid or blood with high reliability and a long service life.

The invention proceeds from ideas of using blood pumps for minimally invasive implantation applications, which are based on the principle of a centrifugal pump with an integrated electric motor for the drive. The required blood flow is produced by means of an impeller. In such systems, the motor should be completely sealed. The torque can be transmitted without contact via a permanent-magnetic coupling (radial rotary coupling). To do this, it is usually necessary to support the impeller radially and axially. A so-called spider bearing comprising recesses or holes for the fluid flow can be provided on the housing side for radial support.

The invention provides a sealed micropump comprising an integrated motor and comprising at least one impeller for producing a fluid flow inside a housing of the micropump, whereby the pump comprises a radial sliding bearing with a spider bearing for supporting an impeller pin of the impeller of the pump inside the housing. The key element of the invention is that the impeller pin has a sheathing made of a material different from that of the spider bearing. The sheathing is fixedly connected to the impeller pin. This configuration allows tribologically advantageous material pairings to be realized for this sliding bearing and at the same time also enables space savings for the bearing arrangement of the impeller pin. In comparison with already known micropumps, said space saving can be used toward enlarging the recesses in the spider bearing surrounding the impeller pin. This has the significant advantage that it reduces pressure losses in this region.

The space required for the radial sliding bearing unavoidably represents a resistance to flow. The solution according to the invention makes it possible to enlarge the openings for the fluid flow in the spider bearing, because there is in particular no need for a bearing bushing inside the central opening of the spider bearing. The frictionally advantageous avoidance of a direct material pairing between the impeller pin and the spider bearing, which are usually both made of metallic materials, for example titanium, by means of an intermediate component made of a different material, in particular plastic, is realized by the sheathing of the impeller pin with such a different material which is provided according to the invention. Overall, this can minimize pressure losses at the radial sliding bearings, which increases the efficiency of the pump. Lower rotational speeds are furthermore possible during operation of the micropump, as a result of which there is less bearing wear overall and the fluid to be conveyed can also be conveyed more gently, so that, for example in the case of an intravascular blood pump, there is less damage to the delicate blood components. All in all, the configuration of the sealed micropump, and in particular the radial sliding bearing for the impeller provided within, enables a significantly reduced flow resistance for the fluid without undermining the reliability and service life of the micropump.

To produce the described sealed micropump, a metallic material is advantageously selected as the material for the impeller pin and for the spider bearing wheel, and the sheathing of the impeller pin is made of a plastic. The impeller pin and the spider bearing can in particular be made of titanium. The sheathing of the impeller pin is preferably made of polyetheretherketone (PEEK).

In a particularly preferred configuration of the sealed micropump, the cross-section of the impeller pin tapers in the region of the sheathing. The available installation space for the spider bearing can thus be increased particularly advantageously. Tapering the impeller pin makes it possible to configure the sheathing of the impeller pin in the bearing region such that there is no increase in the radial cross-section with respect to the region of the impeller pin outside the bearing. The effect on the spider bearing is such that the space required for the bearing bushing provided in conventional solutions inside the spider bearing is entirely available, so that the spider bearing and therefore its passage openings for the fluid can be designed to be correspondingly larger.

In particularly preferred configurations, the sheathing of the impeller pin is formed by a sleeve or a coating, in particular made of plastic, preferably polyetheretherketone, which is firmly and in principle permanently connected to the impeller pin, e.g. by gluing or overmolding. A sleeve having a wall thickness between 0.2 and 0.3 mm, in particular 0.25 mm, is especially suitable. Thinner or thicker layer thicknesses are possible as well. The impeller and the sheathing can form an integral component, whereby the outer diameter of the tribologically loaded impeller pin can be coated. It is possible in principle for the inner diameter of the spider bearing to alternatively or additionally be coated as well.

In another particularly preferred configuration of the micropump, the sheathing of the impeller pin forms a cap which comprises an extension beyond the spider bearing. This extension preferably tapers in upstream direction, thus creating a very advantageous shape in terms of flow, which enables better flow control around the bearing by reducing regions of separation and decreasing the congestion region and thereby contributes to reducing pressure losses and increasing the efficiency of the micropump. For the extension of the cap, conical or semi-ellipsoidal shapes in particular can be preferred.

The sealed micropump can particularly advantageously be a 30 blood pump, in particular an intravascular blood pump for microinvasive applications. The micropump can be a component of a ventricular cardiac support system, for example. The improvements of the micropump proposed here are particularly effective in systems with very small installation space, so that the advantages of the micropumps described here for intravascular blood pumps are an important factor. The outer diameter of the sealed micropump described here is preferably 10 mm or less, so that the requirements for blood pumps to be implanted in a minimally invasive manner are fully taken into account.

Further features and advantages of the invention emerge from the following description of design examples in conjunction with the drawings. The individual features can be realized individually or in combination with one another.

BRIEF DESCRIPTION OF THE DRAWINGS

FIG. 2 shows a longitudinal section through a radial sliding bearing of an impeller pin of the sealed micropump of FIG. 1;

FIG. 3 shows a longitudinal section through a radial sliding bearing of an impeller pin of a sealed micropump in a preferred embodiment of the invention.

DETAILED DESCRIPTION

Figure 1:
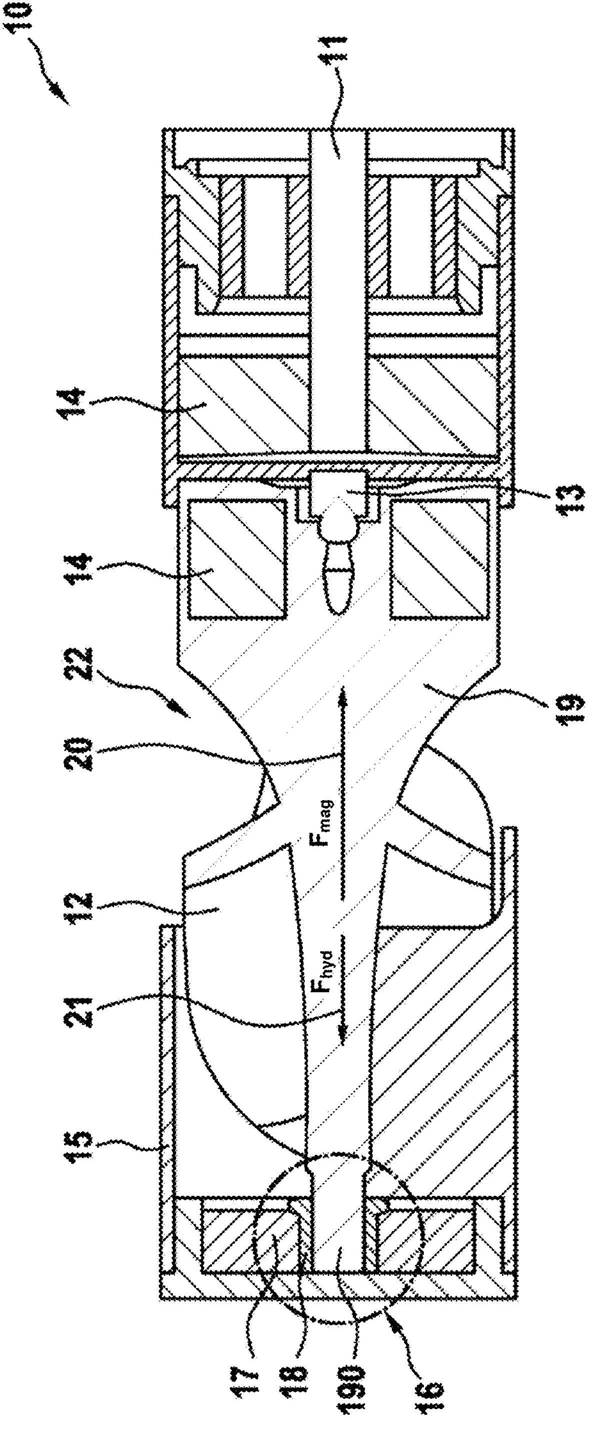
FIG. 1 shows a partial section in longitudinal section of a sealed micropump including an integrated.

FIG. 1 shows the hydraulically active part of a completely sealed micropump 10 according to a current development of such pumps in cross-section. This micropump 10 is in particular intended to be a blood pump for minimally invasive implantations (intravascular blood pump). The micropump 10 is driven by an integrated electric motor, of which the motor shaft 11 is shown here. The rotor or the impeller 19 with the impeller blades (blades) 12 is radially and axially supported via a pivot bearing 13, whereby the torque is transmitted via a permanent-magnetic coupling 14. The required blood flow is produced inside the housing 15 of the sealed blood pump 10 by means of the impeller 19. In a sense, the impeller 19 forms a propeller (impeller) enclosed by a housing. The arrow 20 indicates the magnetically acting forces. The arrow 21 indicates the hydraulically effective forces. The impeller pin 190 (bearing pin) of the impeller 19 is additionally supported via a radial sliding bearing 16 which is located upstream. The radial sliding bearing 16 comprises a spider bearing 17 with a bearing bushing 18 inserted therein and the impeller pin 190 which rotates inside the bearing bushing 18. The bearing bushing 18 is provided to avoid a frictionally unfavorable material pairing between the impeller pin 190 and the spider bearing 17, for example the titanium-titanium material pairing, which is associated with a high degree of wear. The bearing bushing 18 can be made of polyetheretherketone (PEEK), so that the tribologically advantageous PEEK-titanium material pairing is present between the bearing bushing 18 and the impeller pin 190, which is very low friction and wear-resistant.

The blood flow inside the housing 15 is produced by the rotation of the impeller 19. The spider bearing 17 comprises a plurality of inlet openings for the blood. There are nonetheless pressure losses in the region of the spider bearing, because the spider bearing 17 constricts the cross-section thus creating a bottleneck. In the region of the base of the impeller 19, there are openings 22 in the housing 15 of the micropump 10, through which the fluid to be moved, in particular the blood, flows out.

Figures 2, 3:
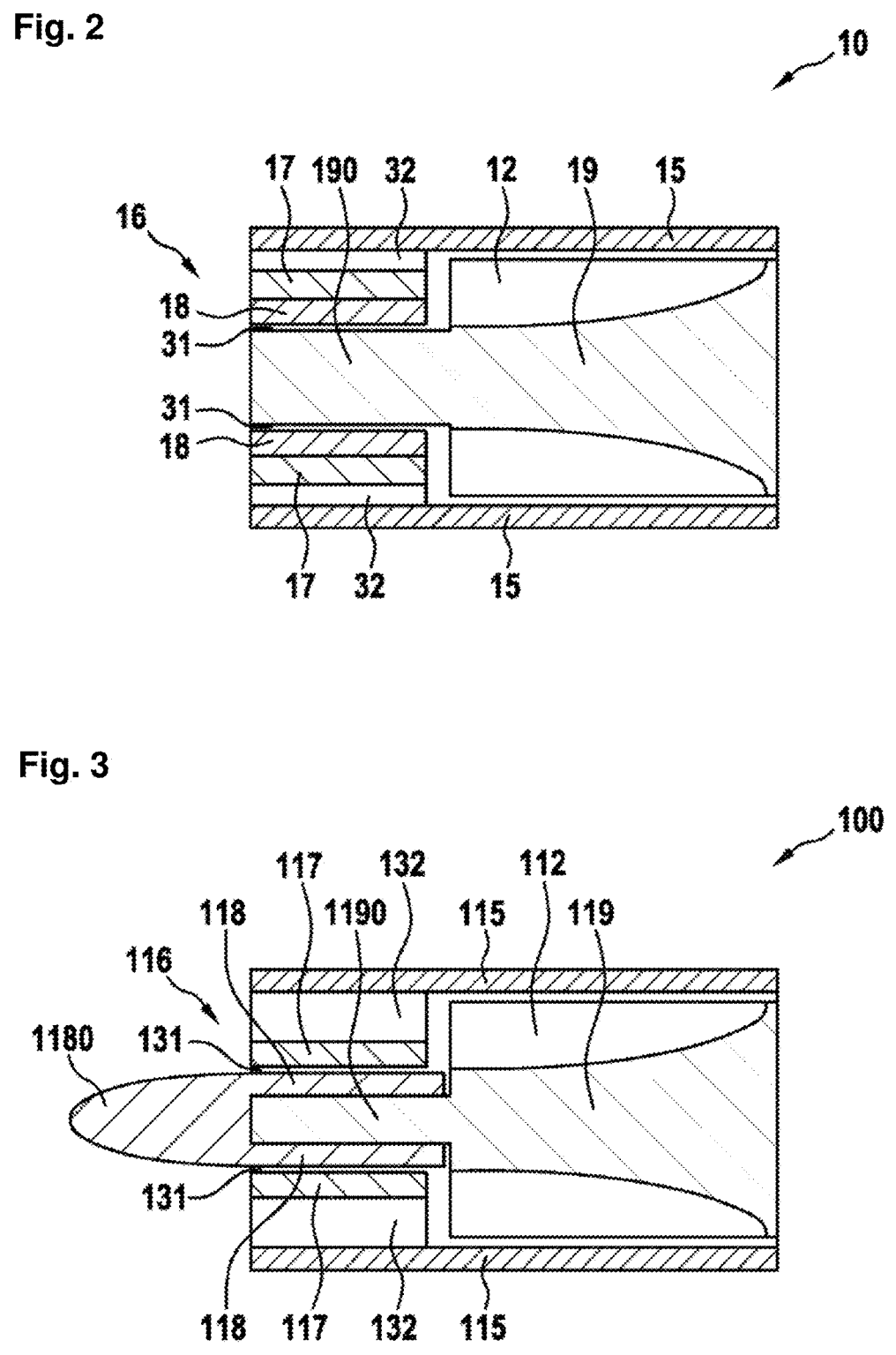

FIG. 2 shows the region of the sliding bearing 16 for the radial support of the impeller pin 190 of the impeller 19 with the impeller blades 12 as a component of a micropump 10 according to FIG. 1 in a schematic longitudinal section. The impeller pin 190 is rotatably mounted inside the bearing bushing 18, whereby a narrow bearing gap 31 is provided between the impeller pin 190 and the bearing bushing 18. The bearing bushing 18 is located inside the spider bearing 17. The regions 32 indicate the openings of the spider bearing 17 through which the fluid, in particular the blood, can flow.

FIG. 3, on the other hand, shows a preferred embodiment of a sealed micropump 100 according to the invention, whereby this figure also shows the region of the sliding bearing 116. The section of the sealed micropump 100 according to the invention shown here shows the impeller pin 1190 of the impeller 119 with the impeller blades 112, whereby the impeller pin 1190 is rotatably mounted in the sliding bearing 116. Inside the housing [150] 115 of the micropump 100, the spider bearing 117 is located in the region of the radial sliding bearing 116. In the region of the sliding bearing 116, the impeller pin 1190 is tapered. The tapering 1190 is surrounded by a sheathing 118. This sheathing 118 is made of a material different from that of the spider bearing 117. The sheathing 118 can, in particular, be made of PEEK and the spider bearing 117 can be made of a metallic material, in particular titanium.

Between the sheathing 118 and the spider bearing 117, there is a narrow bearing gap 131. The impeller pin 1190 sheathed with PEEK therefore rotates in the central recess of the spider bearing 117, thus realizing the tribologically advantageous material pairing of PEEK and titanium, for example. In comparison with a sliding bearing of FIG. 2, in the solution according to the invention the bearing bushing 18 is, in a sense, replaced by the sheathing 118, whereby the overall diameter remains unchanged. As a result of this measure, the space required by the bearing bushing 18 can be used for other purposes, and the openings 132 inside the spider bearing 117, which are provided for the fluid flow, can even be enlarged. Thus, with the same functional bearing dimensions (e.g. bearing diameter 1 mm, bearing gap 10 μm and wall thickness of the sheathing 0.25 mm), there is more cross-section available for the flow.

The sheathing 118 can particularly preferably also be implemented in the form of a cap 1180 which extends the sheathing 118 upstream and, as a result of being suitably shaped, provides advantages in terms of flow. The shape of the cap 1180 can in particular have a diameter that decreases upstream, in particular in a conical or semi-ellipsoidal shape. Improved flow control around the bearing 116 can thus be realized, as a result of which pressure losses are additionally reduced and the efficiency of the micropump 100 is increased.

Figure 4A:
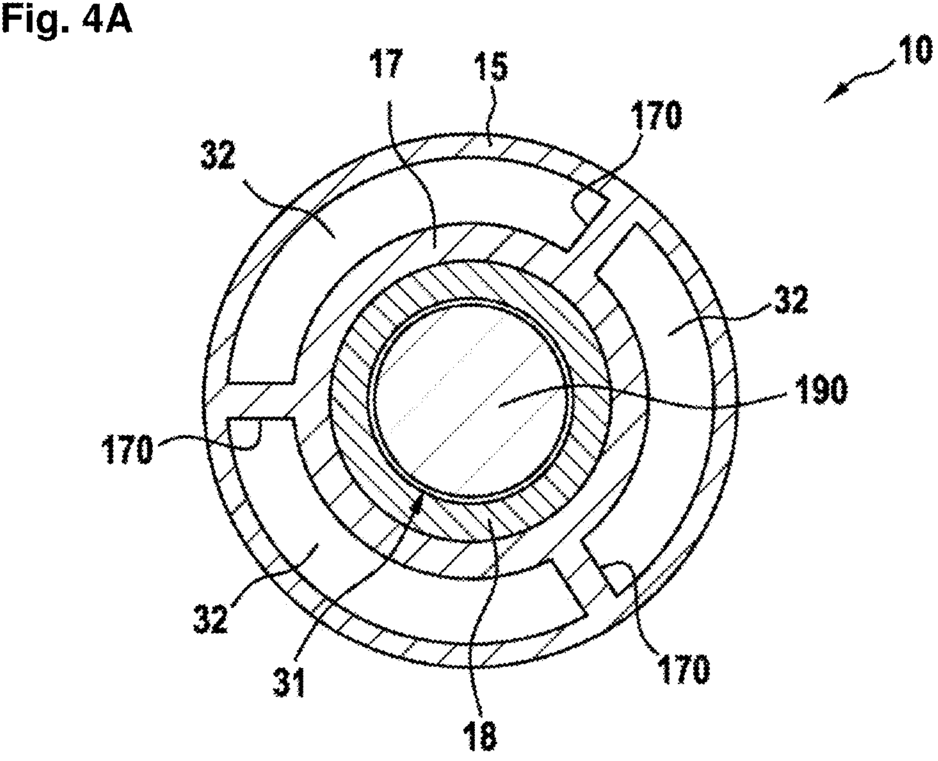
FIGS. 4A and 4B show comparative cross-sections through the radial sliding bearing of FIG. 2 and the radial sliding bearing of FIG. 3, respectively.
Figure 4B:
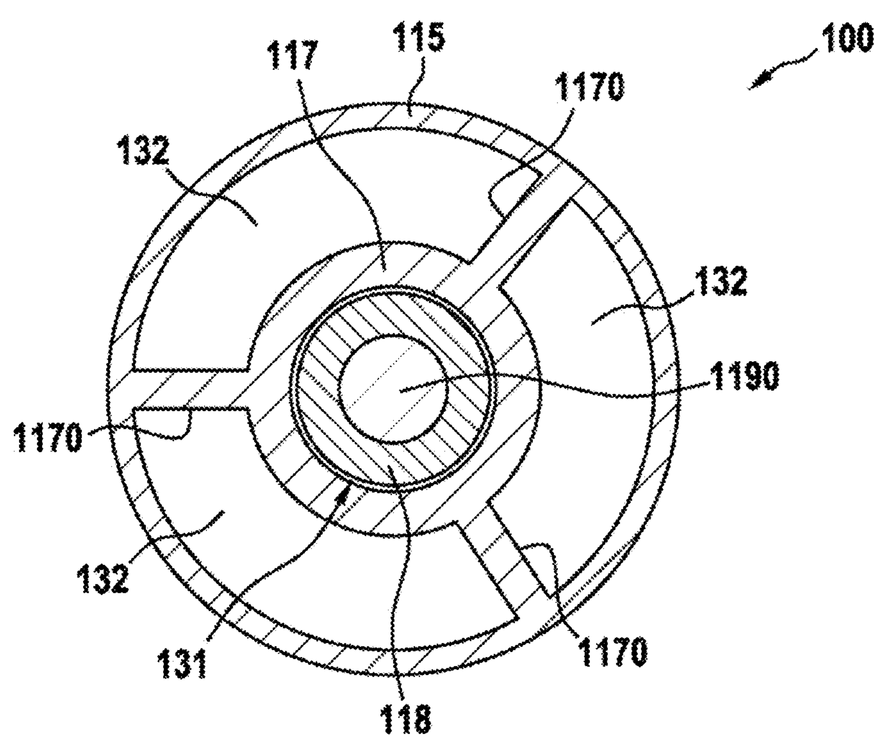

FIGS. 4A and 4B illustrate the configuration of the micropump 100 in the region of the sliding bearing (FIG. 4B) in comparison to the sliding bearing of a micropump 10 of FIG. 1 (FIG. 4A) in cross-section. FIG. 4A shows the sliding bearing with the impeller pin 19, which is rotatably mounted inside the bearing bushing 18, separated by the bearing gap 31. The bearing bushing 18 is located inside the spider bearing 17, which is secured inside the housing 15 of the micropump 10 via the spider bearing struts 170. The space 32 through which the fluid can flow is located between the individual spider bearing struts 170. In comparison, with the configuration according to the invention shown in FIG. 4B, it becomes clear that the corresponding region 132 is significantly enlarged in the solution according to the invention. FIG. 4B shows the tapered region of the impeller pin 1190, which is directly surrounded by the sheathing 118 made of a different material. The narrow bearing gap 131 is located between the sheathing 118 and the interior of the spider bearing 117 (central recess of the spider bearing 17). The interior of the spider bearing 117 is connected to the housing 115 of the micropump 100 via the spider bearing struts 1170. This configuration makes it possible to enlarge the region 132 for fluid flow substantially in comparison to the sliding bearings according to FIG. 1. The micropump 100 according to the invention therefore produces significantly less pressure loss in the upstream region of the radial sliding bearing of the impeller pin.

Such a micropump can be used particularly advantageously as a blood pump for a cardiac support system, for example.

The invention claimed is:

1. A cardiac support system comprising:
- a sealed micropump, the sealed micropump comprising:
  - a housing comprising:
    - an outer wall, and
    - a spider bearing comprising:
      - one or more radial arms extending radially inward from an inner surface of the outer wall; and
      - an annular wall positioned at a radially inward end of the one or more radial arms, the annular wall having a continuous support surface;
  - an integrated motor;
  - at least one impeller operatively coupled to the integrated motor for generating a fluid flow inside the housing of the micropump, wherein the at least one impeller comprises an impeller pin; and
  - a sheathing disposed about and fixedly coupled to the impeller pin, the sheathing having an axial length greater than an axial length of the annular wall;

wherein:
- the sheathing is comprised of a material different from a material of the spider bearing;
- the sheathing is positioned radially between the continuous surface of the annular wall and the impeller pin such that the annular wall surrounds a portion of the sheathing and is configured to support the impeller pin; and
- an interaction between a radially inward surface of the annular wall and a radial outward surface of the sheathing forms a radial sliding bearing.

2. The system of claim 1, wherein the impeller pin and the spider bearing each comprise a metallic material, and wherein the sheathing of the impeller pin comprises a plastic material.

3. The system of claim 1, wherein the impeller pin and the spider bearing each comprise titanium, and wherein the sheathing of the impeller pin comprises polyetheretherketone (PEEK).

4. The system of claim 1, wherein the impeller pin tapers in a region of the sheathing.

5. The system of claim 4, wherein a radial cross-section of the sheathing of the impeller pin in a bearing region is the same as a radial cross-section of the impeller pin outside the bearing region.

6. The system of claim 1, wherein the sheathing of the impeller pin comprises a coating.

7. The system of claim 1, wherein the sheathing of the impeller pin comprises a sleeve.

8. The system of claim 1, wherein the sheathing of the impeller pin extends beyond the spider bearing.

9. The system of claim 8, wherein the sheathing comprises a cap, the cap comprising an extension extending beyond the spider bearing.

10. The system of claim 9, wherein the extension tapers.

11. The system of claim 9, wherein the extension is conical or semi-ellipsoidal.

12. The system of claim 1, wherein the sealed micropump is configured to pump blood.

13. The system of claim 1, wherein an outer diameter of the sealed micropump is at most 10 mm.

14. The system of claim 9, wherein the cap comprises an extension that extends beyond the spider bearing.

15. The system of claim 1, wherein the sheathing comprises a radial outward surface having a constant outer dimension.

* * * * *